US005484570A

United States Patent [19]
Ikeda et al.

[11] Patent Number: 5,484,570
[45] Date of Patent: Jan. 16, 1996

[54] MICROBE PROPAGATION PRENVENTION METHOD

[75] Inventors: Akira Ikeda; Yasuhiro Tanimura; Naoki Nakatsugawa; Masaaki Tanaka, all of Hyogo; Hiroshige Konishi, Shizuoka; Toshie Hiraoka, Shizuoka; Shinji Nishio, Shizuoka; Hiroto Kawahira, Shizuoka, all of Japan

[73] Assignee: Mitsubishi Denki Kabushiki Kaisha, Tokyo, Japan

[21] Appl. No.: 310,715

[22] Filed: Sep. 22, 1994

Related U.S. Application Data

[62] Division of Ser. No. 156,419, Nov. 22, 1993.

[30] Foreign Application Priority Data

| Nov. 24, 1992 | [JP] | Japan | 4-334960 |
| Aug. 31, 1993 | [JP] | Japan | 5-216602 |
| Nov. 12, 1993 | [JP] | Japan | 5-283762 |

[51] Int. Cl.$^6$ ............................................. B01J 19/00
[52] U.S. Cl. .................... 422/1; 422/40; 422/121; 426/236; 426/320; 426/418; 426/419
[58] Field of Search ............................... 422/1, 4, 78, 30, 422/31, 40, 32, 41, 121; 426/236, 418, 419, 320; 250/455.11

[56] References Cited

U.S. PATENT DOCUMENTS

| 2,639,972 | 5/1953  | Hicks | 422/4 |
| 2,851,366 | 9/1958  | Schaefer et al. | 426/236 X |
| 3,910,778 | 10/1975 | Shahgholi et al. | 422/121 X |
| 3,922,349 | 11/1975 | Osborne et al. | 426/236 X |
| 4,133,652 | 1/1979  | Ishikawa et al. | 422/4 X |
| 4,376,642 | 3/1983  | Verity | 422/121 X |
| 4,391,773 | 7/1983  | Flanagan | 422/121 X |
| 4,780,277 | 10/1988 | Tanaka et al. | 422/4 |
| 4,904,289 | 2/1990  | Miyakami et al. | 422/121 X |
| 5,230,220 | 7/1993  | Kang et al. | 422/121 X |

FOREIGN PATENT DOCUMENTS 2823310 12/1978 Germany .............................. 422/236

Primary Examiner—Robert J. Warden
Assistant Examiner—Krisanne M. Thornton
Attorney, Agent, or Firm—Wolf, Greenfield & Sacks

[57] ABSTRACT

A microbe propagation preventing apparatus and a microbe propagation preventing method are provided to prevent anion from decreasing at a time of decomposing ozone generated by gaseous discharge or ionization so as to sufficiently generate air ion, and to sufficiently prevent propagation of microbes adhering to an object by using the air ion without secondary pollution. Further, in the apparatus and the method, a gas containing the ion is supplied into water so as to prevent the microbe propagation in the water. In the apparatus, an ozone decomposing chamber is mounted to be electrically insulated from an air duct. An electrode to remove a positive ion is mounted to obtain only a negative ion, and extend a lifetime of the obtained ion. An ion supplying portion is mounted to supply an ionized gas into a space housing the object in which microbes can be propagated, and return the ionized gas to an ionization chamber. Further, a diffusing apparatus is provided to transform the ionic gas into bubbles so as to feed the bubbles into the water in the water reservoir.

6 Claims, 22 Drawing Sheets

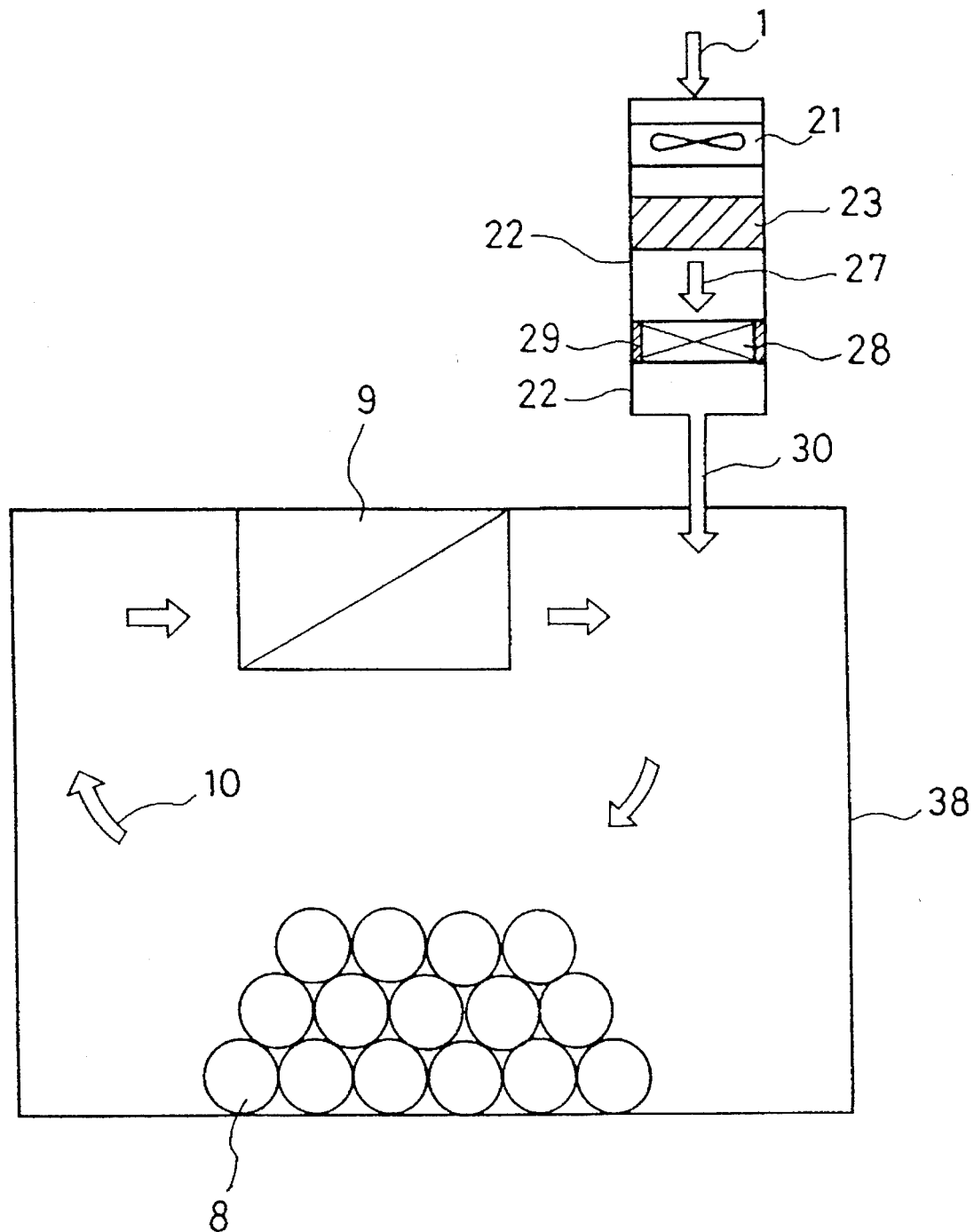
F I G. 7

FIG. 8

| | ION PROCESSING | NO PROCESSING | OZONE PROCESSING |
|---|---|---|---|
| CONCENTRATION (/cm$^3$) | ABOUT 10$^4$ | | ABOUT 3 × 10$^{13}$ (1 ppm) |
| APPEARANCE | GOOD NO VARIATION | SLIGHT DISCOLORATION INTO BLACK (DEGRADED FRESHNESS) | DISCOLORATION INTO DARK-RED DUE TO OZONE OXIDATIVE EFFECT (DEGRADED QUALITY) |
| ODOR | ODORLESS | PUTRID SMELL | ODORLESS |
| NUMBER OF GENERAL BACTERIA (/cm$^2$) | ABOUT 20 | ABOUT 200 | ABOUT 30 |

F I G. 9

| | ION PROCESSING | NO PROCESSING | OZONE PROCESSING |
|---|---|---|---|
| CONCENTRATION (/cm³) | ABOUT $10^4$ | | ABOUT $3 \times 10^{11}$ (0.01 ppm) |
| NUMBER OF BACTERIA (/PETRI DISH) | ABOUT 10 | ABOUT 370 | ABOUT 350 |

F I G. 10

| | ION PROCESSING | NO PROCESSING | OZONE PROCESSING |
|---|---|---|---|
| CONCENTRATION (/cm³) | ABOUT $10^4$ | | ABOUT $3 \times 10^{11}$ (0.01 ppm) |
| NUMBER OF MOLD (/PETRI DISH) | ABOUT 10 | ABOUT 100 | ABOUT 110 |

F I G. 12
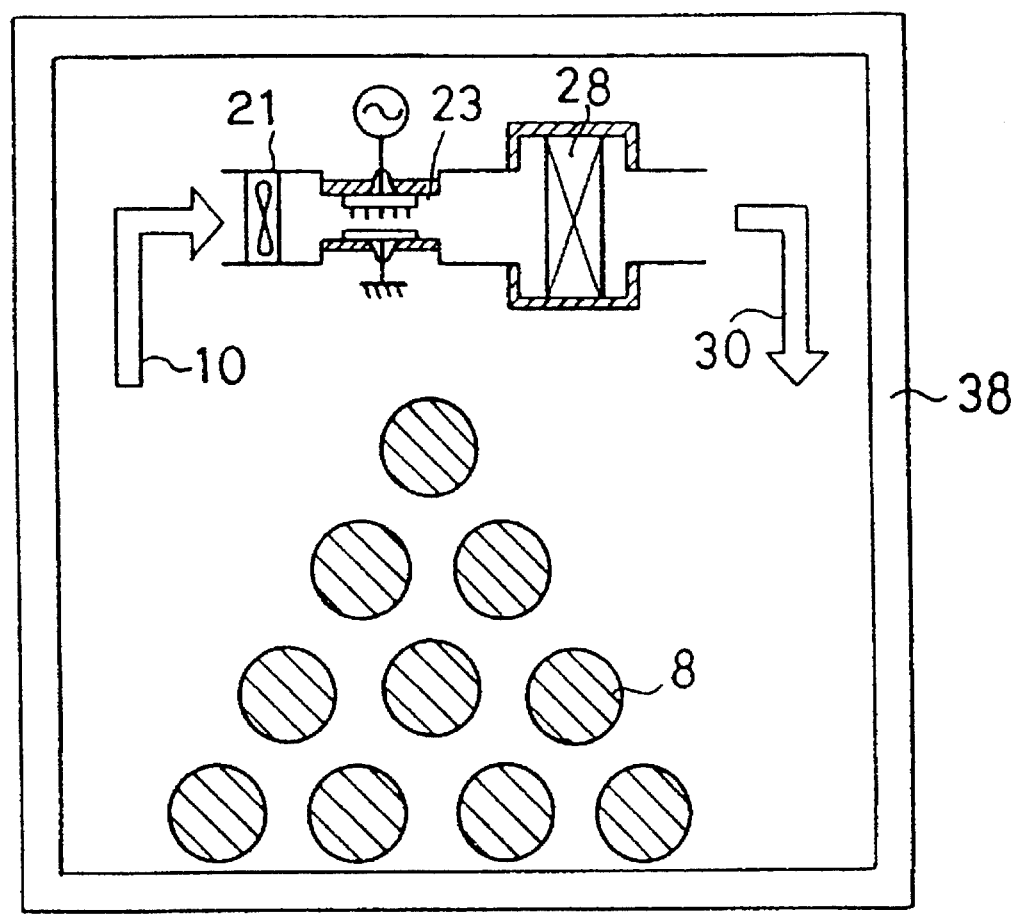

F I G. 13
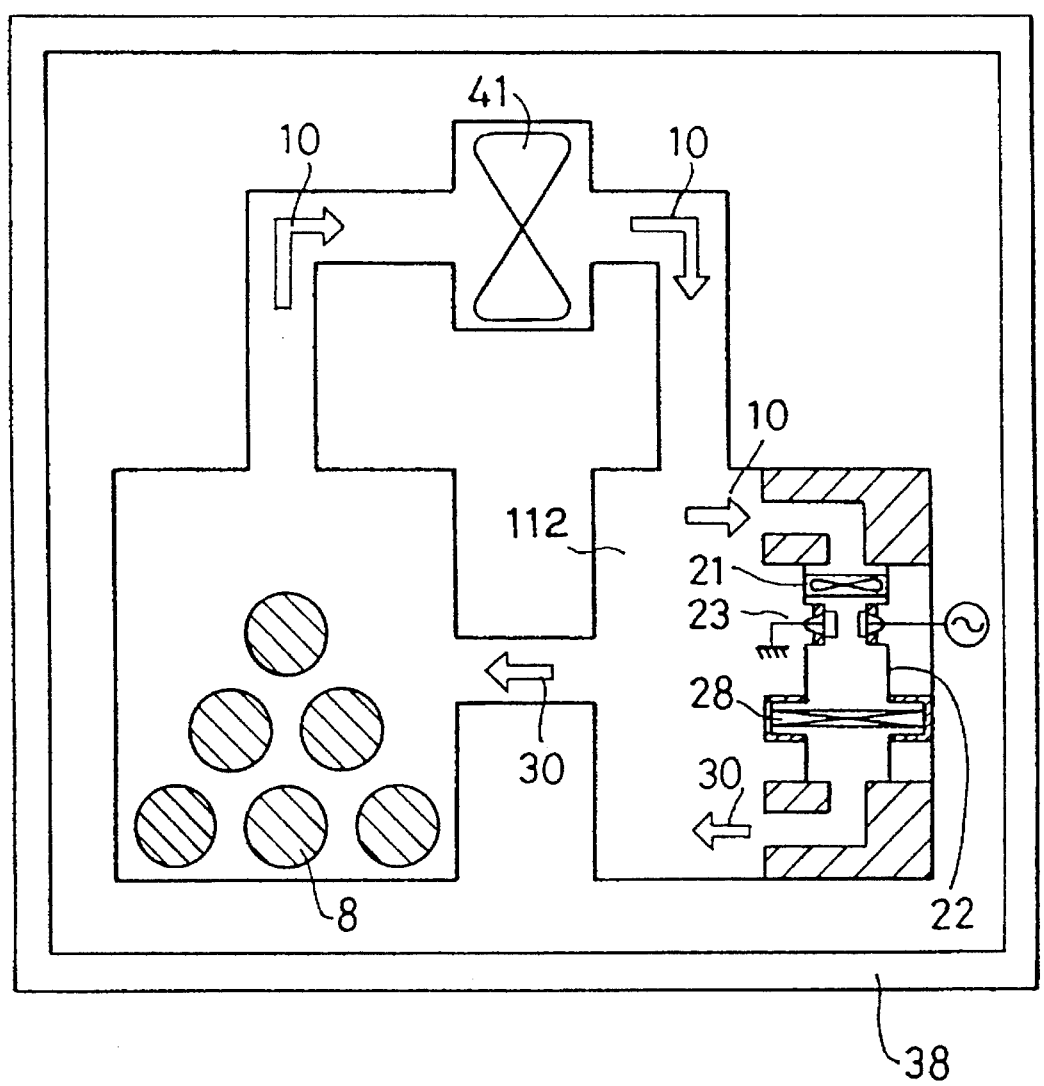

MICROBE PROPAGATION PRENVENTION METHOD

This application is a division of application Ser. No. 08/156,419 filed on Nov. 22, 1993.

BACKGROUND OF THE INVENTION

1. Field of the Invention

The present invention relates to a microbe propagation preventing apparatus and a microbe propagation preventing method which enable prevention of microbe propagation in foods or the like by using ions.

2. Description of the Prior Art

FIG. 29 is a perspective view showing a conventional microbe propagation preventing apparatus disclosed in, for example, Japanese Patent Application Laid-Open No. 3-72289. In FIG. 29, reference numeral 1 means an external gas, 2 is a metallic needle electrode made of metallic material such as tungsten, stainless steel, or nickel, 3 is a metallic grid-like electrode, 4 is a high voltage generator to apply high voltage between the metallic needle electrode 2 and the metallic grid-like electrode 3 so as to generate corona discharge, 5 is an ozone decomposing catalyst to decompose ozone contained in the gas 1, and 6 is an ionized gas containing no ozone.

A description will now be given of the operation.

A distance (a gap length) between the metallic needle electrode 2 and the metallic grid-like electrode 3 is set at several centimeters. When the high voltage generator 4 is used to apply dc high voltage in a range of several to over ten but less than twenty kilovolts between the metallic needle electrode 2 and the metallic grid-like electrode 3, the metallic grid-like electrode 3 is positively charged, and the metallic needle electrode is negatively charged. Thereby, an electric field having high intensity is generated at a distal end of a needle of the metallic needle electrode 2, resulting in glow-like discharge having a light color which is called the corona discharge. Thus, the corona discharge negatively ionizes an oxygen molecule in the air in an ionization space. While the negative ion generated by the corona discharge travels to the metallic grid-like electrode 3, ambient air is also carried because of viscosity of the air. As a result, an ionized air flows from the metallic needle electrode 2 toward the metallic grid-like electrode 3.

However, since the external gas 1 contains the oxygen molecule, the corona discharge generates ozone as well as the negative ion. In this connection, high concentration of ozone is harmful because the ozone exhibits intensive oxidization.

Hence, the ozone decomposing catalyst 5 is disposed on the downstream side in an air duct through which the gas containing the ozone flows. The ozone decomposing catalyst 5 removes the ozone from the ionized gas so that the ionized air 6 containing no ozone is discharged into a space.

Since the inventors found that the gas 6 can reduce the propagation of the microbes adhering objects such as foods in case the gas 6 contains an appropriate concentration of ion, the prior art apparatus has been discussed as a microbe propagation preventing apparatus. However, prior to filing of this application, the prior art apparatus is actually disclosed as simply an apparatus to generate ions rather than the apparatus to prevent the microbe propagation by using the ions. A detailed description thereof will be given later.

Alternatively, there is another embodiment as shown in FIG. 30, in which a gas containing the ozone is provided for foods housed in a refrigerator so as to prevent the propagation of the microbe generated in the foods.

In FIG. 30, reference numeral 7 means the refrigerator, 8 means the foods housed in the refrigerator 7, 9 is a cooler of the refrigerator 7, 10 is a gas in the refrigerator 7, 11 is a fan to draw the gas 10, 12 is an ozonizer to generate the ozone by the discharge, 13 is an ozone sterilizing/deodorizing chamber to sterilize and deodorize the microbes such as bacteria, mold and a malodorous component which are contained in the gas 10, 14 is the ozone decomposing catalyst to decompose excess ozone by using, for example, manganese dioxide, and 15 is a clean gas which is sterilized and deodorized.

A description will now be given of the operation.

The refrigerator 7 includes the cooler 9 to cool the inside of the refrigerator 7 in which the foods 8 are housed. On the other hand, the ozonizer 12 injects the ozone to the gas 10 drawn by the fan 11 including the mold, the bacteria, or the malodorous component such that ozone concentration in the gas 10 is approximately multiple ppm. In such a way, the ozone is injected into the gas 10, and the gas 10 is introduced into the ozone sterilizing/deodorizing chamber 13 so as to sterilize or deodorize the mold, the bacteria, or the malodorous component which is contained in the gas 10.

However, the gas 10 in the ozone sterilizing/deodorizing chamber 13 contains the ozone with concentration approximately multiple ppm. Consequently, when the gas 10 is discharged as it is, the gas 10 is harmful for a human body. Further, there is a risk in that equipments such a heat exchanger, or the fan 11 may corrode due to the ozone (specifically, if the ozone concentration in the refrigerator 7 is increased to a range no less than 0.1 ppm, some kinds of foods may discolor or deteriorate, and the equipments such as the heat exchanger, the fan 11 in the refrigerator 9 corrode). Hence, the gas 10 including relatively high concentration of ozone is introduced into the ozone decomposing catalyst 14 to decompose and remove the ozone so as to reduce the ozone concentration to a range no more than an operation reference value (of 0.1 ppm). Thereafter, the gas 10 is discharged as the clean gas 15 into the refrigerator 7.

The conventional microbe propagation preventing apparatus is constructed as set forth above, that is, the conventional apparatus is not provided for purpose of the prevention of the microbe propagation by using the ion. Further, when the ozone is decomposed by the ozone decomposing catalyst 5, a generating negative ion contacts a case body of the ozone decomposing catalyst 5 to recombine with the case body since the ozone decomposing catalyst 5 includes the metallic case body. As a result, there are several problems in that, for example, the microbe propagation can not sufficiently be prevented due to the reduction of the generating negative ion.

On the other hand, in case microbe propagation is prevented by using the ozone, it is necessary to reduce the ozone concentration in the gas 10 to the range no more than 0.1 ppm in view of adverse effects to the human body. Accordingly, there are other problems in that, for example, the microbe propagation can not sufficiently be prevented in the reduced ozone concentration.

SUMMARY OF THE INVENTION

In view of the foregoing, it is an object of the present invention to provide a microbe propagation preventing apparatus in which reduction of ion can be avoided when ozone is decomposed so as to sufficiently prevent microbe propagation.

It is another object of the present invention to provide a microbe propagation preventing apparatus in which any one of a negative ion and a positive ion can be generated.

It is still another object of the present invention to provide a microbe propagation preventing apparatus in which an ionized gas is supplied into a space housing a certain object so as to prevent microbe propagation in the object.

It is a still further object of the present invention to provide a microbe propagation preventing apparatus in which an ionized gas is supplied into a water reservoir storing certain liquid so as to prevent microbe propagation in the liquid.

It is a still further object of the present invention to provide a microbe propagation preventing method in which microbe propagation can be prevented in a space housing an object in which the microbe can be propagated.

According to the first aspect of the present invention, for achieving the above-mentioned objects, there is provided a microbe propagation preventing apparatus in which an ozone decomposing chamber is mounted to be electrically insulated from an air duct.

As stated above, in the microbe propagation preventing apparatus according to the first aspect of the present invention, the ozone decomposing chamber is mounted to be electrically insulated from the air duct. Consequently, a generating negative ion never recombines with a case body of the ozone decomposing chamber even if the negative ion contacts the case body. As a result, there is no reduction of the generating negative ion in the ozone decomposing chamber.

According to the second aspect of the present invention, there is provided a microbe propagation preventing apparatus in which an air duct is made of an insulating material.

As stated above, in the microbe propagation preventing apparatus according to the second aspect of the present invention, the air duct is made of the insulating material. Consequently, a generating negative ion never recombines with the air duct even if the negative ion contacts the air duct. As a result, there is no reduction of the generating negative ion in the ozone decomposing chamber.

According to the third aspect of the present invention, there is provided a microbe propagation preventing apparatus in which an ozone decomposing chamber includes a grid-like heating resistor which is coated with an insulating material.

As stated above, in the microbe propagation preventing apparatus according to the third aspect of the present invention, the ozone decomposing chamber includes the grid-like heating resistor which is coated with the insulating material. As a result, there is no reduction of the generating negative ion in the ozone decomposing chamber.

According to the fourth aspect of the present invention, there is provided a microbe propagation preventing apparatus in which a case body of an ozone decomposing chamber is made of an insulating material.

As stated above, in the microbe propagation preventing apparatus according to the fourth aspect of the present invention, the case body of the ozone decomposing chamber is made of the insulating material. Consequently, a generating negative ion never recombines with the case body of the ozone decomposing chamber even if the negative ion contacts the case body. As a result, there is no reduction of the generating negative ion in the ozone decomposing chamber.

According to the fifth aspect of the present invention, there is provided a microbe propagation preventing apparatus in which an air duct is surrounded by a heat insulating material.

As stated above, in the microbe propagation preventing apparatus according to the fifth aspect of the present invention, the air duct is surrounded by the heat insulating material. As a result, it is possible to reduce a decrease of temperature of an ionized gas so as to promote decomposition of ozone.

According to the sixth aspect of the present invention, there is provided a microbe propagation preventing apparatus in which moisture removing means for removing moisture in a gas ionized by an ionization chamber is provided on the upstream side of the ionization chamber.

As stated above, in the microbe propagation preventing apparatus according to the sixth aspect of the present invention, the moisture removing means for removing the moisture in the gas ionized by the ionization chamber is provided on the upstream side of the ionization chamber. As a result, it is possible to reduce an amount of the moisture contained in the gas so as to promote generation of an ion.

According to the seventh aspect of the present invention, there is provided a microbe propagation preventing apparatus in which a pair of conductive nets are disposed parallel to each other at a predetermined interval between an ionization chamber and an ozone decomposing chamber, a dc power source being provided to apply positive dc voltage to one conductive net disposed on the downstream side in the pair of conductive nets, and the other conductive net disposed on the upstream side being grounded.

As stated above, in the microbe propagation preventing apparatus according to the seventh aspect of the present invention, the pair of conductive nets are disposed parallel to each other at the predetermined interval between the ionization chamber and the ozone decomposing chamber, the dc power source being provided to apply the positive dc voltage to one conductive net disposed on the downstream side in the pair of conductive nets, and the other conductive net disposed on the upstream side being grounded. As a result, it is possible to remove a positive ion, and obtain only a negative ion.

According to the eighth aspect of the present invention, there is provided a microbe propagation preventing apparatus in which a pair of conductive nets are disposed parallel to each other at a predetermined interval between an ionization chamber and an ozone decomposing chamber, a dc power source being provided to apply negative dc voltage to one conductive net disposed on the downstream side in the pair of conductive nets, and the other conductive net disposed on the upstream side being grounded.

As stated above, in the microbe propagation preventing apparatus according to the eighth aspect of the present invention, the pair of conductive nets are disposed parallel to each other at the predetermined interval between the ionization chamber and the ozone decomposing chamber, the dc power source being provided to apply the negative dc voltage to one conductive net disposed on the downstream side in the pair of conductive nets, and the other conductive net disposed on the upstream side being grounded. As a result, it is possible to remove a negative ion, and obtain only a positive ion.

According to the ninth aspect of the present invention, there is provided a microbe propagation preventing apparatus in which, in a pair of conductive nets, one conductive net disposed on the downstream side has a coarser mesh than that of the other conductive net disposed on the upstream side.

As stated above, in the microbe propagation preventing apparatus according to the ninth aspect of the present invention, one conductive net disposed on the downstream side has a coarser mesh than that of the other conductive net disposed on the upstream side in the pair of conductive nets. As a result, the obtained ion never decreases.

According to the tenth aspect of the present invention, there is provided a microbe propagation preventing apparatus in which an ionic gas from which ozone is removed by an ozone decomposing chamber is supplied into a space housing an object in which microbes can be propagated.

As stated above, in the microbe propagation preventing apparatus according to the tenth aspect of the present invention, the ionic gas from which the ozone is removed by the ozone decomposing chamber is supplied into the space housing the object in which the microbes can be propagated. Consequently, an ionized gas can be supplied for the object.

According to the eleventh aspect of the present invention, there is provided a microbe propagation preventing apparatus in which an ionic gas from which ozone is removed by an ozone decomposing chamber is supplied into a space housing an object in which microbes can be propagated, and the gas supplied into the space being returned to an ionization chamber.

As stated above, in the microbe propagation preventing apparatus according to the eleventh aspect of the present invention, the ionic gas from which the ozone is removed by the ozone decomposing chamber is supplied into the space housing the object in which the microbes can be propagated, and the gas supplied into the space being returned to the ionization chamber. Consequently, an ionized gas can be supplied to the object, and an odor of the gas can be deodorized.

According to the twelfth aspect of the present invention, there is provided a microbe propagation preventing apparatus including an ion supplying portion having a space to house an object in which microbes can be propagated, and supplying the space with an ionic gas from which ozone is removed by an ozone decomposing chamber.

As stated above, the microbe propagation preventing apparatus according to the twelfth aspect of the present invention including the ion supplying portion having the space to house the object in which the microbes can be propagated, and supplying the space with the ionic gas from which ozone is removed by the ozone decomposing chamber. As a result, an ionized gas can be supplied for the object.

According to the thirteenth aspect of the present invention, there is provided a microbe propagation preventing apparatus including an ion supplying portion having a space to house an object in which microbes can be propagated, supplying the space with an ionic gas from which ozone is removed by an ozone decomposing chamber, and returning the gas supplied into the space to an ionization chamber.

As stated above, the microbe propagation preventing apparatus according to the thirteenth aspect of the present invention including the ion supplying portion having the space to house the object in which the microbes can be propagated, supplying the space with the ionic gas from which ozone is removed by the ozone decomposing chamber, and returning the gas supplied into the space to the ionization chamber. As a result, an ionized gas can be supplied for the object, and an odor of the gas can be deodorized.

According to the fourteenth aspect of the present invention, there is provided a microbe propagation preventing apparatus in which an ionization chamber includes a pair of electrodes, and negative dc voltage being applied to the electrodes so as to ionize an electron.

As stated above, in the microbe propagation preventing apparatus according to the fourteenth aspect of the present invention, the ionization chamber includes the pair of electrodes, and negative dc voltage being applied to the electrodes so as to ionize the electron. It is thereby possible to obtain only a negative ion.

According to the fifteenth aspect of the present invention, there is provided a microbe propagation preventing apparatus in which an ion supplying portion includes a space whose inner surface is made of an insulating material.

As stated above, in the microbe propagation preventing apparatus according to the fifteenth aspect of the present invention, the ion supplying portion includes the space whose inner surface is made of the insulating material. As a result, a generating ion never decreases in the ion supplying portion.

According to the sixteenth aspect of the present invention, there is provided a microbe propagation preventing apparatus in which an ionic gas from which ozone is removed by an ozone decomposing chamber is transformed into bubbles to be supplied into water of a water reservoir.

As stated above, in the microbe propagation preventing apparatus according to the sixteenth aspect of the present invention, the ionic gas from which the ozone is removed by the ozone decomposing chamber is transformed into bubbles to be supplied into the water in the water reservoir. It is thereby possible to reduce microbe propagation in the water.

According to the seventeenth aspect of the present invention, there is provided a microbe propagation preventing apparatus including gas mixer to mix ozone generated from an ozonizer with a gas ionized by an ionization chamber, and a gas-liquid mixer to transform a gas mixed by the gas mixer into bubbles so as to feed the bubbles into water in a water reservoir.

As stated above, the microbe propagation preventing apparatus according to the seventeenth aspect of the present invention including the gas mixer to mix ozone generated from the ozonizer with the gas ionized by the ionization chamber, and the gas-liquid mixer to transform the gas mixed by the gas mixer into bubbles so as to feed the bubbles into water in the water reservoir. As a result, it is possible to surely reduce microbe propagation in the water because of a synergistic effect of an ion and the ozone, and to sterilize microbes.

According to the eighteenth aspect of the present invention, there is provided a microbe propagation preventing apparatus in which a gas-liquid mixer includes a diffuser.

As stated above, in the microbe propagation preventing apparatus according to the eighteenth aspect of the present invention, the gas-liquid mixer includes the diffuser. It is thereby possible to reduce microbe propagation in water as in the sixteenth aspect and the seventeenth aspect.

According to the nineteenth aspect of the present invention, there is provided a microbe propagation preventing apparatus in which a gas-liquid mixer includes an ejector.

As stated above, in the microbe propagation preventing apparatus according to the nineteenth aspect of the present invention, the gas-liquid mixer includes the ejector. It is thereby possible to reduce microbe propagation in water as in the sixteenth aspect and the seventeenth aspect.

According to the twentieth aspect of the present invention, there is provided a microbe propagation preventing method in which an ionic gas from which ozone is removed by an ozone decomposing chamber is supplied into a space housing an object in which microbes can be propagated.

As stated above, in the microbe propagation preventing method according to the twentieth aspect of the present invention, the ionic gas from which ozone is removed by the ozone decomposing chamber is supplied into the space housing the object in which the microbes can be propagated. As a result, an ionized gas can be supplied for the object.

According to the twenty-first aspect of the present invention, there is provided a microbe propagation preventing method in which an ionic gas from which ozone is removed by an ozone decomposing chamber is supplied into a space housing an object in which microbes can be propagated, and the ionic gas supplied into the space being returned to an ionization chamber.

As stated above, in the microbe propagation preventing method according to the twenty-first aspect of the present invention, the ionic gas from which the ozone is removed by the ozone decomposing chamber is supplied into the space housing the object in which microbes can be propagated, and the ionic gas supplied into the space being returned to the ionization chamber. As a result, an ionized gas can be supplied for the object, and an odor of the gas can be deodorized.

According to the twenty-second aspect of the present invention, there is provided a microbe propagation preventing method in which, when an ionic gas from which ozone is removed by an ozone decomposing chamber is supplied into a space, the ionic gas is intermittently supplied into the space.

As stated above, in the microbe propagation preventing method according to the twenty-second aspect of the present invention, when the ionic gas from which the ozone is removed by the ozone decomposing chamber is supplied into the space, the ionic gas is intermittently supplied into the space. It is thereby possible to reduce microbe propagation in the space as in the case of continuous supply of the ionic gas.

According to the twenty-third aspect of the present invention, there is provided a microbe propagation preventing method in which, when an ionic gas from which ozone is removed by an ozone decomposing chamber is supplied into a space, the ionic gas is supplied after the gas is humidified.

As stated above, in the microbe propagation preventing method according to the twenty-third aspect of the present invention, when the ionic gas from which the ozone is removed by the ozone decomposing chamber is supplied into the space, the ionic gas is supplied after the gas is humidified. It is thereby possible to reduce microbe propagation while preventing drying of an object such as a food contained in the space.

According to the twenty-fourth aspect of the present invention, there is provided a microbe propagation preventing method in which a wind blower draws a gas in a closed space which prevents microbe propagation, and supplies an ionic gas from which ozone is removed by an ozone decomposing chamber to the space.

As stated above, in the microbe propagation preventing method according to the twenty-fourth aspect of the present invention, the wind blower draws the gas in the closed space which prevents microbe propagation, and supplies the ionic gas from which the ozone is removed by the ozone decomposing chamber to the space. As a result, it is possible to reduce the microbe propagation in the closed space.

According to the twenty-fifth aspect of the present invention, there is provided a microbe propagation preventing method in which an ionic gas from which ozone is removed by an ozone decomposing chamber is supplied to an opened space or liquid which prevents microbe propagation, and an excess ion being removed from the space or the liquid.

As stated above, in the microbe propagation preventing method according to the twenty-fifth aspect of the present invention, the ionic gas from which the ozone is removed by the ozone decomposing chamber is supplied into the opened space or the liquid which prevents the microbe propagation, and the excess ion being removed from the space or the liquid. As a result, it is possible to reduce the excess ion supplied to the space or the liquid while preventing the microbe propagation.

According to the twenty-sixth aspect of the present invention, there is provided a microbe propagation preventing method in which an excess ion in a space or liquid is removed by a conductive net which is grounded.

As stated above, in the microbe propagation preventing method according to the twenty-sixth aspect of the present invention, the excess ion in the space or liquid is removed by the conductive net which is grounded. As a result, it is possible to reduce the excess ion supplied to the space or the liquid in a simple configuration requiring no replacement.

The above and further objects and novel features of the invention will more fully appear from the following detailed description when the same is read in connection with the accompanying drawing. It is to be expressly understood, however, that the drawings are for purpose of illustration only and are not intended as a definition of the limits of the invention.

BRIEF DESCRIPTION OF THE DRAWINGS

FIG. 7 is a diagram showing a configuration of a microbe propagation preventing apparatus according to the embodiment 10 of the present invention;

FIG. 8 is a table showing experimental results of an experiment carried out to prove that microbe propagation can be reduced by an ion;

FIG. 9 is a table showing experimental results of an experiment carried out to prove that bacteria propagation can be reduced by the ion;

FIG. 10 is a table showing experimental results of an experiment carried out to prove that propagation of mold adhering a strawberry can be reduced by the ion;

FIG. 12 is a diagram showing a configuration of the microbe propagation preventing apparatus according to the embodiment 11 of the present invention;

FIG. 13 is a diagram showing a configuration of the microbe propagation preventing apparatus according to the embodiment 11 of the present invention;

DETAILED DESCRIPTION OF THE PREFERRED EMBODIMENTS

Preferred embodiments of the invention will now be described in detail referring to the accompanying drawings.

Embodiment 1

A description will now be given of the operation.

Figure 1:
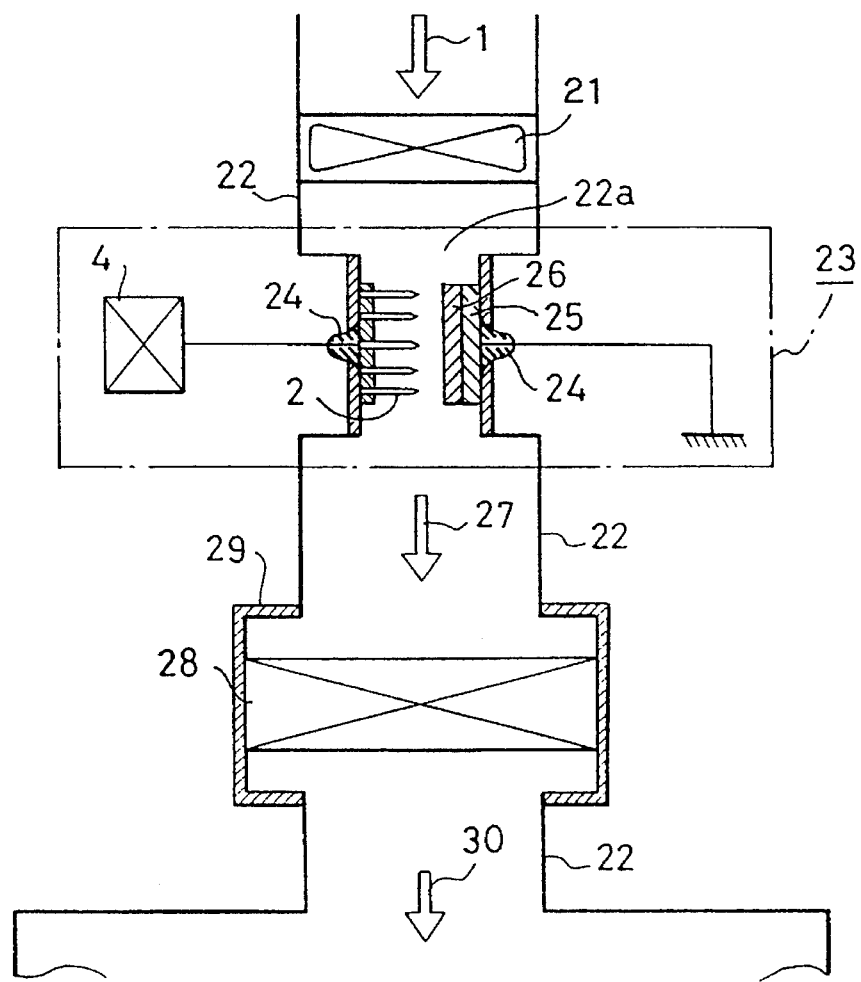
FIG. 1 is a diagram showing a configuration of a microbe propagation preventing apparatus according to the embodiment 1 of the present invention.

FIG. 1 is a diagram showing a configuration of a microbe propagation preventing apparatus according to the embodiment 1 of the present invention. In FIG. 1, the same reference numerals are used for component parts identical with or equivalent to those in a conventional apparatus, and descriptions thereof are omitted.

Reference numeral 21 means a fan (an air blower), 22 means an air duct through which a gas 1 drawn by the fan 21 passes, 22a is a supply port to draw the gas 1, 23 is an ionization chamber mounted in the air duct 22 to ionize electrons with respect to the gas 1 so as to ionize the gas 1, 24 is a bushing made of an insulating material, 25 is a metallic flat earth electrode which is disposed opposite to a metallic needle electrode 2, 26 is a flat dielectric which is deposited on or tightly attached to the metallic flat earth electrode 25, and is made of a dielectric material such as ceramic, glass, or quartz.

Further, reference numeral 27 means a gas ionized by the ionization chamber 23, and 28 is an ozone decomposing chamber which is mounted in the air duct 22 to decompose the ozone contained in the gas 27 ionized by the ionization chamber 23 so as to remove the ozone from the gas 27. The ozone decomposing chamber 28 is filled with an ozone decomposing catalyst such as manganese dioxide, active carbon, or activated alumina. Reference numeral 29 means an insulator to electrically insulate the ozone decomposing chamber 28 from the air duct 22. In the embodiment 1, the partial air duct 22 includes the insulating material, that is, the insulating material is used for the air duct 22 around only a position at which the ozone decomposing chamber 28 is mounted. For example, the air duct 22 is made of an organic insulating material such as polyethylene, polyvinyl chloride, or acryl resin, or made of an inorganic insulating material such as glass, or quartz. Reference numeral 30 means an ionized gas containing no ozone.

A description will now be given of the operation.

First, the fan 21 draws the external gas 1 through the supply port 22a so that the gas 1 is introduced into the ionization chamber 23 through the air duct 22.

The ionization chamber 23 includes the plurality of metallic needle electrodes 2, and the metallic flat earth electrode 25 tightly attached to the dielectric 26 which is disposed opposite to the metallic needle electrodes 2. In this case, for example, a distance (a gap length) between the metallic needle electrodes 2 and the metallic flat earth electrode 25 tightly attached to the dielectric 26 is set to several millimeters, and ac voltage of several kilovolts is applied between both the electrodes. Accordingly, an electric field having high intensity is established at a distal end of the metallic needle electrode 2 so that discharge of the electron occurs.

Therefore, when the gas 1 is introduced into the ionization chamber 23 in the discharge, the electron collides with oxygen molecules or the like contained in the gas 1 to ionize the oxygen molecules or the like, resulting in the ionic gas 1.

However, if the gas 1 contains the oxygen molecule, the discharge concurrently generates the ozone as well as the ion so that the ionized gas 27 contains the ozone.

The ozone can exhibit strong oxidization, and is harmful when the ozone concentration is equal to a predetermined value or more. Hence, the ozone decomposing chamber 28 decomposes the ionized gas 27 containing the ozone to remove the ozone so as to discharge the ionized gas 30 containing no ozone into a space.

In this connection, as set forth above, the ozone decomposing catalyst 5 has a metallic case body in a conventional embodiment. When the ozone is decomposed by the ozone decomposing catalyst 5, the generating ion contacts the case body to recombine with the case body (i.e., the ion is neutralized). As a result, there is a problem in that the generating ion decreases. In the embodiment 1, the ozone decomposing chamber 28 is electrically insulated from the air duct 22 by the insulator 29 as shown in FIG. 1. Thus, unlike the conventional embodiment, the ion generated in the ionization chamber 23 never exhibits recombination in the ozone decomposing chamber 28, and there is little reduction of the ion.

Accordingly, it is possible to discharge a large amount of the ionized gas 30 into, for example, a space housing objects or the like in which the microbe can be propagated so as to reduce the microbe propagation in the objects or the like (in an illustrative experiment, it was proven that the ionized gas 30 can reduce the microbe propagation. This experiment will be discussed later).

A description will now be given of one illustrative experiment which was carried out to prove that the ion generated in the microbe propagation preventing apparatus hardly decreases in the ozone decomposing chamber 28.

In the illustrative experiment, there were disposed five metallic needle electrodes 2 having a length of 1 cm at intervals of 5 mm, the gap length was set at 4 mm between the metallic needle electrodes 2 and the metallic flat earth electrode 25 having a width of 1 cm and a length of 3 cm, and the dielectric 26 having a thickness of 0.5 mm was tightly attached to the metallic flat earth electrode 25. Further, zero peak voltage of ac voltage applied between both the electrodes was set at 3.5 kV, wind velocity of the air passing between both the electrodes was set at about 0.2 m/s. The ozone decomposing chamber 28 was mounted in the air duct 22 at a position of the insulator 29 made of the insulating material such as acryl resin, a temperature of supplied air was set at 5° C., and humidity thereof was set at 95%.

In such a condition, the ion is generated so as to measure the ion concentration of the ionized gas 27 by using an ion concentration meter. As a result, the ion concentration at an outlet of the ionization chamber 23 was about $10^6$ ions/cm$^3$, and the ion concentration of the ionized gas 30 immediately after passing through the ozone decomposing chamber 28 was about $10^5$ ions/cm$^3$.

As set forth above, in case the ozone decomposing chamber 28 was mounted at the air duct 22 including the insulator 29, the ion concentration in the ionized gas 30 passing through the ozone decomposing chamber 28 was reduced to about one-tenth of the ion concentration before the ionized gas 30 passes through the ozone decomposing chamber 28. However, the ion concentration in the ionized gas 30 was hundred times or more than ion concentration in normal air (i.e., 800 to 1000 ions/cm$^3$). Further, the ion concentration in the ionized gas 30 was tens times ion concentration in case the ozone decomposing chamber 28 is directly mounted in the air duct 22 made of a metallic material such as stainless as in the conventional apparatus.

On the other hand, the ozone was concurrently generated by the discharge, and the ionized gas 27 on the upstream side of the ozone decomposing chamber 28 contained the ozone ranging from about 0.2 to 0.4 ppm. However, after the ionized gas 30 passed through the ozone decomposing chamber 28, the ion concentration of the ionized gas 30 was 0.01 ppm or less (i.e., equal to or less than a limit of detection in a potassium iodide method in accordance with the JIS (Japanese Industrial Standard)).

As seen from the facts as described above, according to the embodiment 1, it is possible to remove the ozone while maintaining a sufficient ion concentration in the ionized gas 30.

Though five needles of the metallic needle electrode 2 were provided for 3 cm$^2$ area of the metallic flat earth electrode 25 in the above illustrative experiment, it is possible to increase an amount of the generating ion if the number of the needles are increased. However, since the increase of the needles results in an increased amount of the generating ozone, it is necessary to increase a thickness of the ozone decomposing catalyst in the ozone decomposing chamber 28.

Further, though the maximum voltage of the applied ac voltage, i.e., the zero peak voltage was set at 3.5 kV, it is possible to increase the amount of the generating ion if the applied voltage is more increased. However, the amount of the generating ozone also increases concurrently. In case of the gap length of 4 mm, when the zero peak voltage was in a range of several to about 10 kilovolts, the amount of the generating ion more increased as the applied voltage was more increased.

Short-circuit occurred for the gap length of 2 mm or less in case the maximum value of the ac voltage, i.e., the zero peak voltage was set at 3.5 kV. Hence, at least the gap length of 3 mm or more was required. Since the amount of the generating ion more increases as the gap length is more reduced, the gap length is preferably in a range of 3 to 5 mm.

The air having the wind velocity of 0.2 m/s was supplied between both the electrodes in the illustrative experiment. Further, when the wind velocity of the air was varied in a range of 0.1 to 2.0 m/s, it was found that the amount of the generating ion more increased as the wind velocity was more increased.

Though the insulating material made of the acryl resin was employed as the insulator 29 in the illustrative experiment, it was also possible to provide the same effect by using another insulating material such as polyethylene, polyvinyl chloride, glass, or quartz glass.

The above illustrative experiment has been discussed with reference to a case where the air was employed as the gas 1. When gaseous oxygen was employed as the gas 1, an amount of ion contained in the ionized gas 30 becomes several times that of ion in the air.

Further, though the dielectric 26 made of the ceramic was provided between the metallic needle electrode 2 and the metallic flat earth electrode 25 in the illustrative experiment, it was also possible to provide the same effect by using another dielectric made of quartz or glass.

In addition, in the above illustrative experiment, the discharge occurring at a time of applying ac high voltage was used as ion generating means in the ionization chamber 23. However, it was also possible to provide the same effect by removing the dielectric 26, and using the discharge occurring at a time of applying dc high voltage for generation of the ion.

Moreover, it was also possible to provide the same effect by generating the ions by means such as irradiation, or light.

Figure 28:
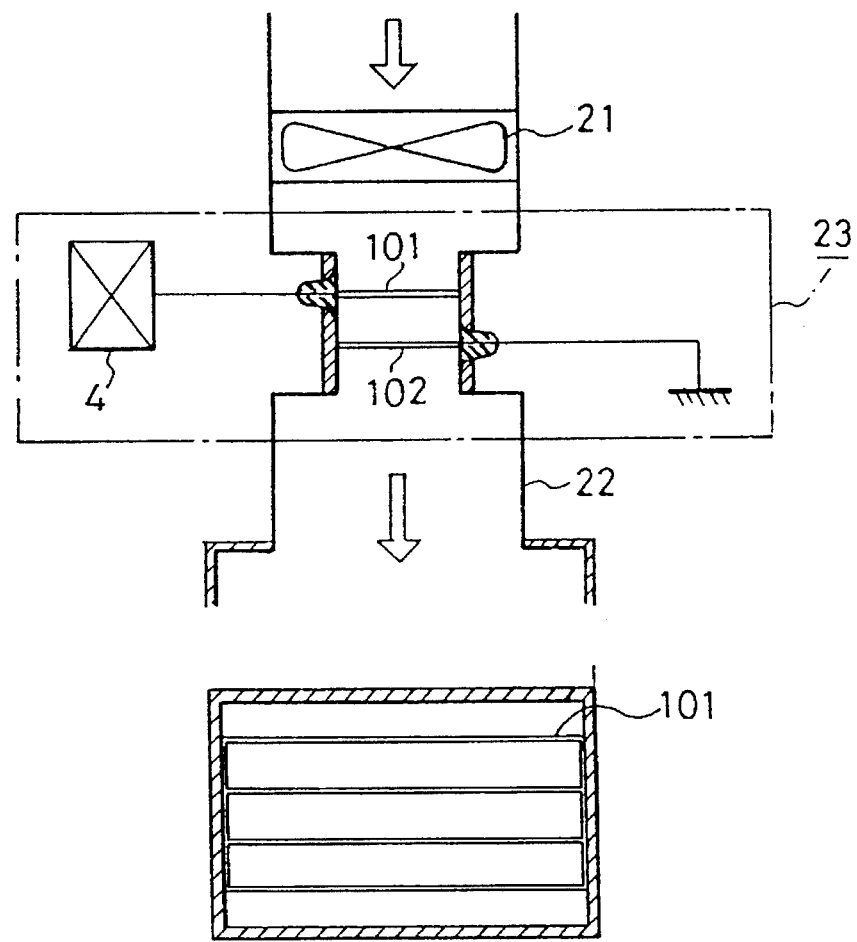
FIG. 28 is a diagram showing a configuration of an ionization chamber.
Figure 29:
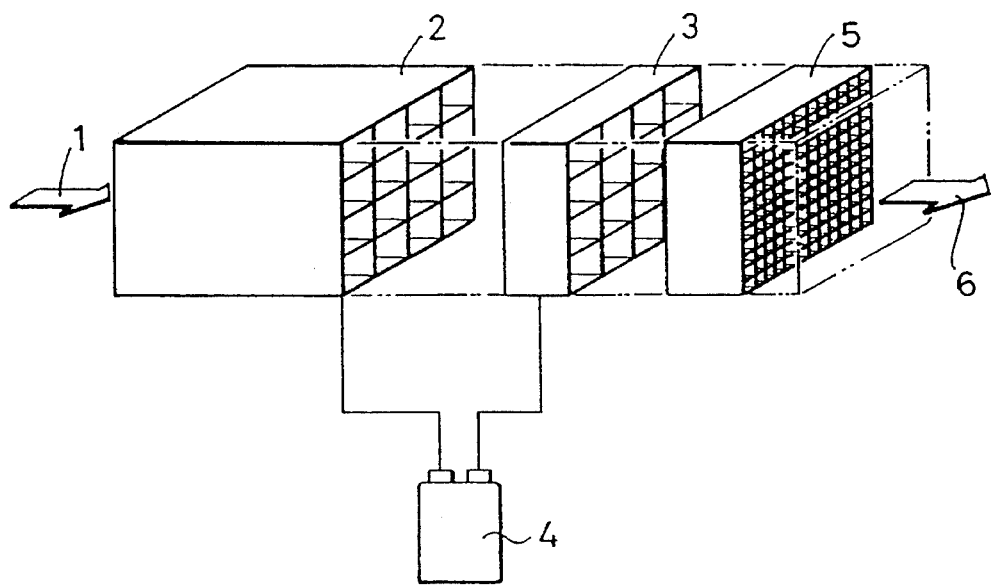
FIG. 29 is a perspective view showing a conventional microbe propagation preventing apparatus.

Furthermore, in the embodiment, the metal flat earth electrode 25 is tightly attached to the dielectric 26 which is opposed to the metallic needle electrode 2 in the ionization chamber 23. However, as shown in FIG. 28, there may be provided a plurality of metallic fine wires 101 having diameters in an approximate range of 0.1 to 0.2 mm or a plurality of metallic fine wires 101 which are coated with a film dielectric, and a metallic grid-like electrode 102 opposed to the metallic fine wire in the ionization chamber 23. It was also possible to provide the same effect by generating the ions by using discharge occurring at a time of applying high voltage ac or high voltage dc to the plurality of metallic fine wires 101.

Embodiment 2

Figure 2:
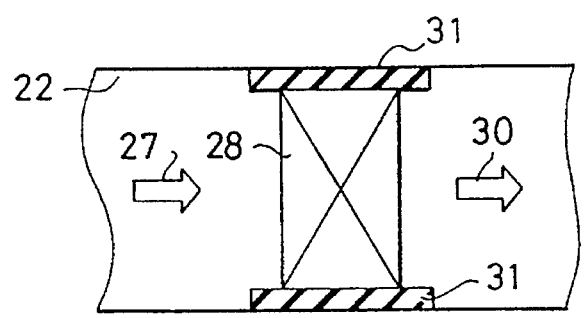
FIG. 2 is a sectional view showing an ozone decomposing chamber which is mounted through an insulator.

In the embodiment 1, an air duct 22 partially includes an insulator 29, and an ozone decomposing chamber 28 is mounted in the partial air duct 22. However, the air duct 22 itself may be made of metal, and an insulator 31 made of an insulating material such as acryl resin, polyethylene, polyvinyl chloride, glass, or quartz glass may be interposed between the air duct 22 and the ozone decomposing chamber 28 as shown in FIG. 2, resulting in the same effect as that in the embodiment 1.

Embodiment 3

Figure 3:
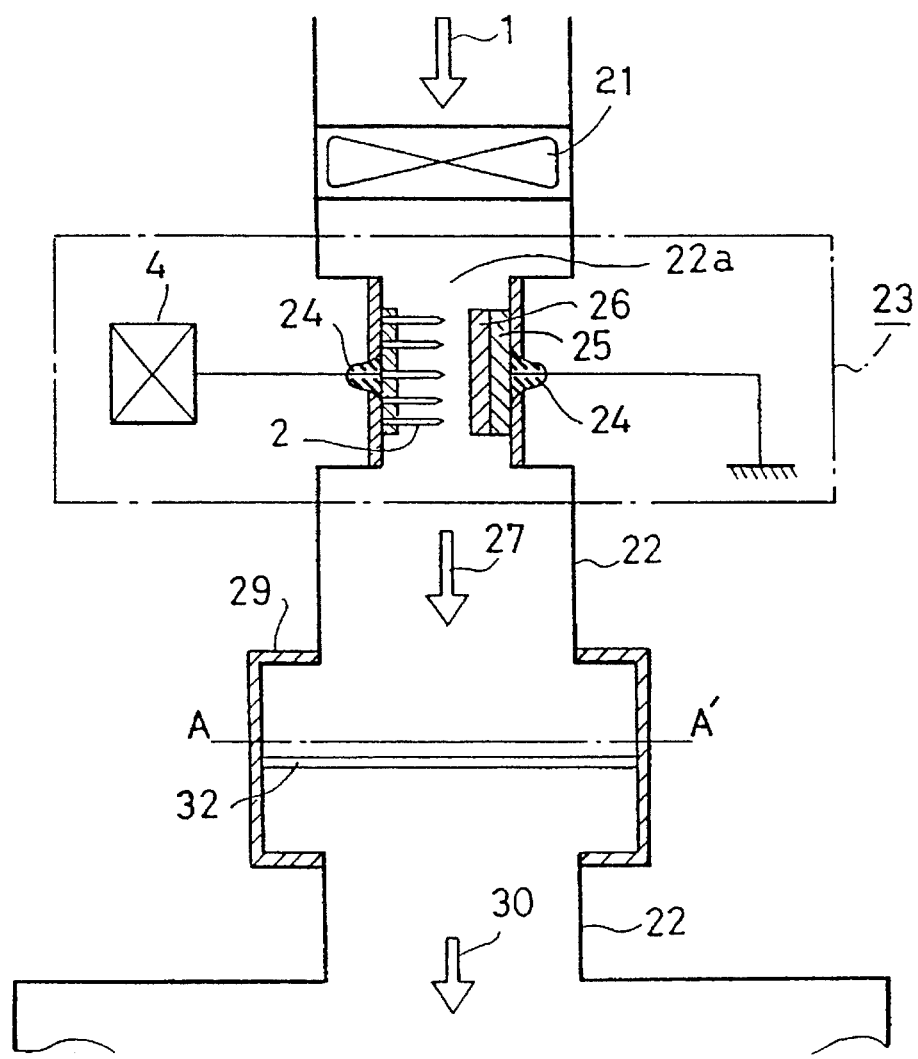
FIG. 3 is a diagram showing a configuration of a microbe propagation preventing apparatus according to the embodiment 3 of the present invention.
Figure 3:
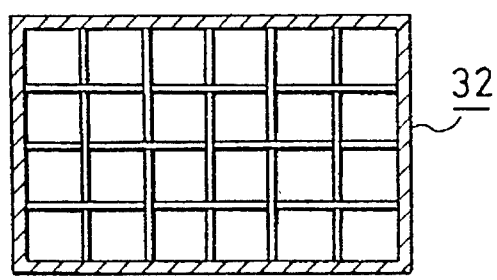

In the embodiment 1, an ozone decomposing chamber 28 is filled with an ozone decomposing catalyst such as manganese dioxide, active carbon, or activated alumina. However, the ozone decomposing chamber 28 may include a grid-like heating resistor 32 which is coated with an organic insulating material such as Teflon resin or acryl resin, or an inorganic insulating material such as ceramic material as shown in FIG. 3 so as to pyrolytically decompose ozone.

Embodiment 4

In the embodiment 1, an air duct 22 partially includes an insulator 29, and an ozone decomposing chamber 28 is mounted in the partial air duct 22. However, the air duct 22 itself may be made of metal, and a case body of the ozone decomposing chamber 28 may be made of an insulating material, resulting in the same effect as that in the embodiment 1.

Embodiment 5

Figure 4:
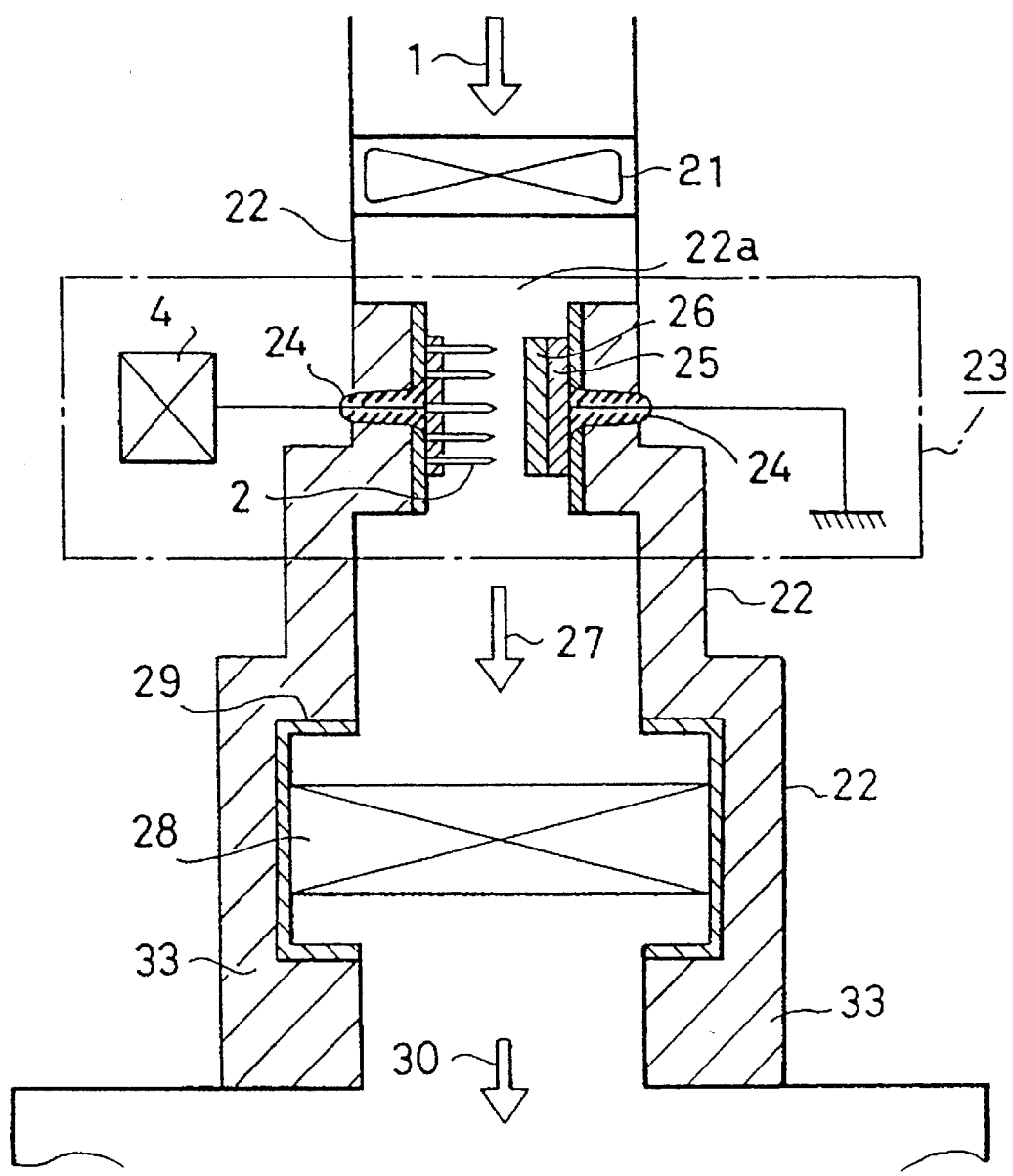
FIG. 4 is a diagram showing a configuration of a microbe propagation preventing apparatus according to the embodiment 5 of the present invention.

FIG. 4 is a diagram showing a configuration of a microbe propagation preventing apparatus according to the embodiment 5 of the present invention. In FIG. 4, reference numeral 33 means a heat insulating material provided for an outer periphery of an air duct 22 to prevent circumferential radiation of heat which is generated at a time of ion generation in an ionization chamber 23.

According to the embodiment 5, heat dissipation in the air duct 22 can be prevented. Therefore, it is possible to reduce a decreased temperature of an ionized gas 27 containing ozone, and promote decomposition of the ozone.

Embodiment 6

Figure 5:
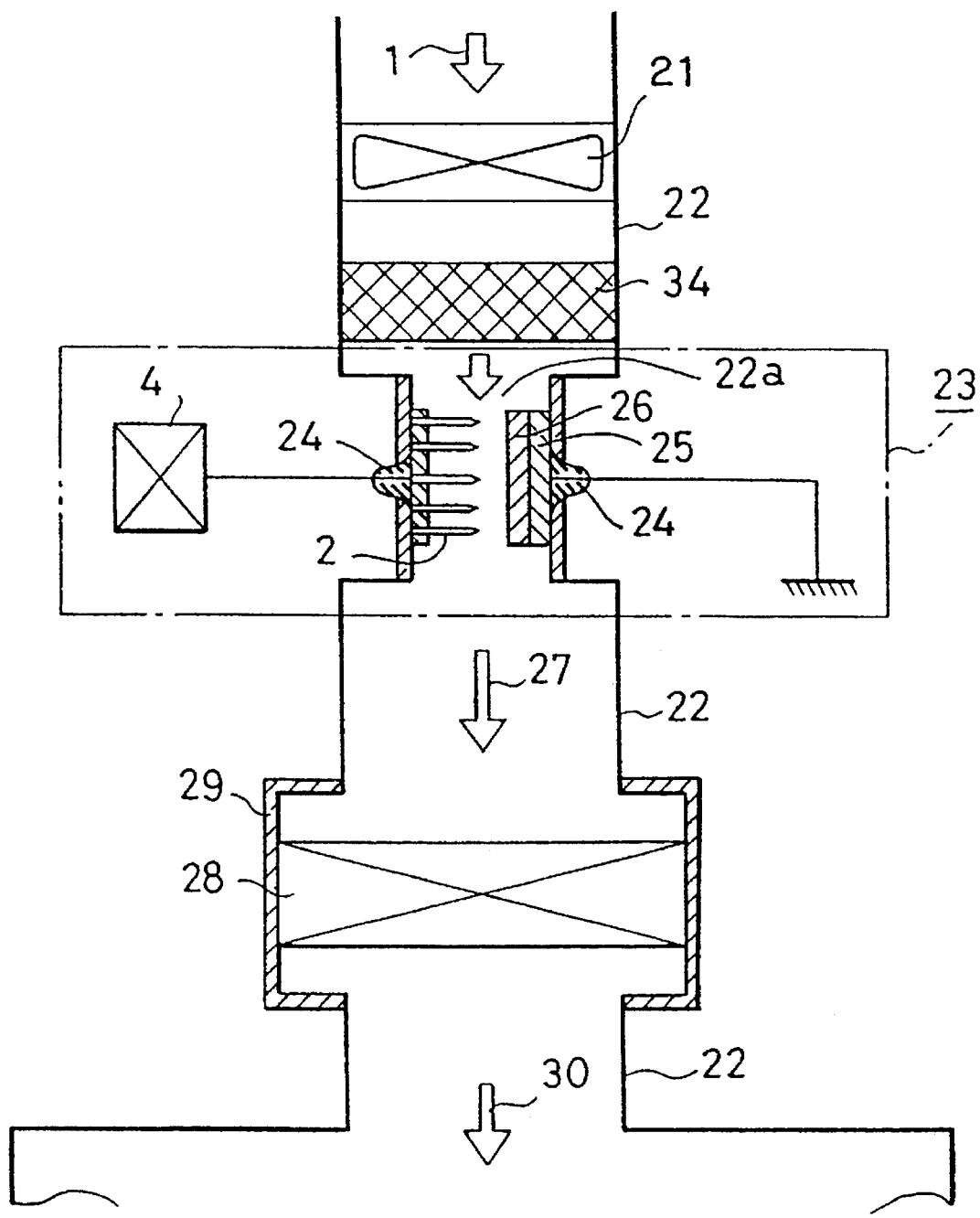
FIG. 5 is a diagram showing a configuration of a microbe propagation preventing apparatus according to the embodiment 6 of the present invention.

FIG. 5 is a diagram showing a configuration of a microbe propagation preventing apparatus according to the embodiment 6 of the present invention. In FIG. 5, reference numeral 34 means a drying chamber (moisture removing means) which is mounted on the upstream side of an ionization chamber 23 to remove moisture contained in a gas 1 drawn by a fan 21.

The drying chamber 34 in the embodiment 6 is filled with adsorbent such as silica gel so that the moisture in the gas 1 drawn by the fan 21 can be removed, and a dried gas can be introduced into the ionization chamber 23.

An amount of ions generated in the ionization chamber 23 is inversely proportional to an amount of moisture contained in the gas 1. Consequently, it is possible to increase the amount of generating ion by an amount of the gas 1 dried in the drying chamber 34 as compared with the embodiment 1. For example, when the gas 1 having a temperature of 25° C. passes through the drying chamber 34 to reduce relative humidity from 90% to 40%, the amount of generating ion can considerably be increased.

Embodiment 7

Figure 6:
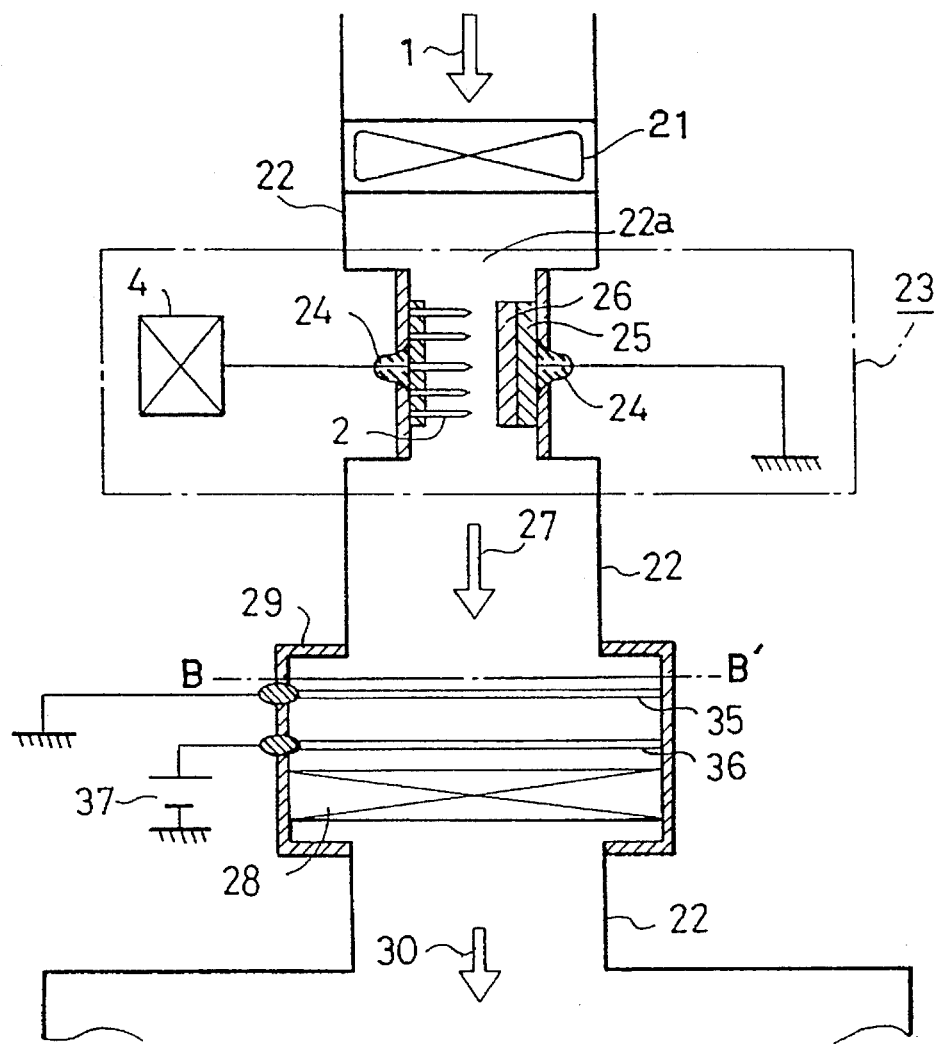
FIG. 6 is a diagram showing a configuration of a microbe propagation preventing apparatus according to the embodiment 7 of the present invention.
Figure 6:
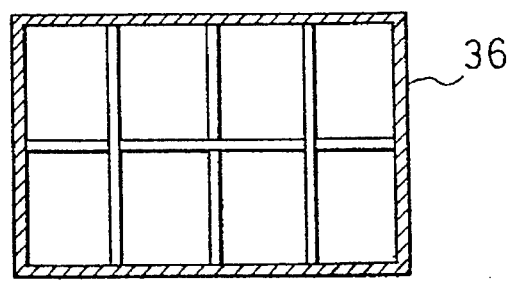

FIG. 6 is a diagram showing a configuration of a microbe propagation preventing apparatus according to the embodiment 7 of the present invention. In FIG. 6, reference numeral 35 means a metallic net (a conductive net) disposed between an ionization chamber 23 and an ozone decomposing chamber 28, and the metallic net 35 is grounded. Reference numeral 36 means a metallic net (a conductive net) which is disposed parallel to the metallic net 35 at a predetermined interval on the downstream side of the metallic net 35, and 37 means a dc power source to apply positive dc voltage to the metallic net 36.

A description will now be given of the operation.

In the embodiment 1, ions are generated by applying ac voltage of several kilovolts between a metallic needle electrode 2 and a metallic flat earth electrode 25 in the ionization chamber 23, resulting in generation of a negative ion and a positive ion respectively having substantially the same amount.

Accordingly, in the embodiment 1, it is difficult to selectively obtain only the negative ion having an excellent effect of preventing microbe propagation from the apparatus. However, in the embodiment 6, it is possible to selectively obtain only the negative ion from the apparatus.

As in the embodiment 1, when high ac voltage of several kilovolts is applied between the metallic needle electrode 2 and the metallic flat earth electrode 25, discharge of electron occurs in the ionization chamber 23 to ionize a gas 1. As set forth above, the positive ion is generated by an impact ionization action of the electron, and the negative ion is generated by an adhering action of the electron. The gas 1 contains the positive and negative ions respectively having substantially the same amount.

An ionized gas 27 is introduced into the pair of metallic nets 35, 36 which are disposed in an air duct 22 between the ionization chamber 23 and the ozone decomposing chamber 28. As shown in FIG. 6(b), the metallic nets 35 and 36 are provided in a grid-like form having a coarse mesh of about 10 in mesh so that the ionized gas 27 can easily pass through the nets.

Further, positive dc voltage in the range of tens to hundreds volts is applied to the metallic net 36 by the dc power source 37, resulting in establishment of an electric field in a direction from the metallic net 36 to the metallic net 35 between the metallic nets 35 and 36.

Therefore, when the ionized gas 27 containing ozone flows into the electric field, the electric field causes the positive ion to move toward the grounded metallic net 35, and disappear after collision with the metallic net 35. On the other hand, the negative ion moves toward the metallic net 36 to which positive dc voltage is applied. The metallic net 36 has the coarse mesh, and the negative ion moves in the same direction as that of flow of the gas 27. Accordingly, the negative ion can pass through the metallic net 36 by using the flow of the gas 27 without collision with the metallic net 36, resulting in no loss of the negative ion.

In such a way, it is possible to remove the ozone from the ionized gas 27 containing the ozone and the negative ion by the ozone decomposing chamber 28, and discharge an ionized gas 30 containing only the negative ion.

The embodiment 7 has been discussed with reference to a case where the pair of metallic nets 35 and 36 are mounted at the interval of several centimeters, and the dc voltage in the range of tens to hundreds volts is applied to the pair of metallic nets 35, 36. However, the interval between the metallic nets 35 and 36, and a value of the applied dc voltage may be adjusted so as to generate electric field intensity in the range of tens of thousands of volts/m to over hundred of thousands but less than two hundred of thousands of volts/m between the pair of metallic nets 35 and 36.

Embodiment 8

In the embodiment 7, positive dc voltage is applied by a dc power source 37 to remove a positive ion so as to obtain only a negative ion. According to the same principle as that in the embodiment 7, it is also possible to remove the negative ion and obtain only the positive ion by the dc power source 37 applying negative dc voltage.

In case only the positive ion is selectively obtained, there is an effect in that a lifetime of remaining ions becomes longer than that would be in case both the positive and negative ions are concurrently obtained. This is true for a case only the negative ion is obtained.

In this connection, the positive ion causes rooting of a plant, and serves as a growth promotor.

Embodiment 9

The embodiment 7 has been discussed with reference to a case where metallic nets 35 and 36 have the same coarse mesh. If the metallic net 36 has a coarser mesh than that of the metallic net 35, possibility of collision of ions with the metallic net 36 is reduced so that a loss of the selectively obtained ion can be further reduced. Specifically, the metallic net 36 may have a coarser mesh than that of the metallic net 35 by about one in mesh, resulting in reduction of the loss.

Embodiment 10

FIG. 7 is a diagram showing a configuration of a microbe propagation preventing apparatus according to the embodiment 10 of the present invention. In FIG. 7, reference numeral 38 means a refrigerator (an ion supplying portion) including a space housing foods (objects) 8 in which microbes can be propagated, and supplying the space with an ionic gas 30 from which ozone is removed by an ozone decomposing chamber 28.

A description will now be given of the operation.

The refrigerator 38 is cooled by a cooler 9 at a temperature ranging from 0° to about 5° C. When a fan 21 is operated in this condition, as in the embodiment 1, the ozone decomposing chamber 28 generates the ionized gas 30 containing no ozone. Consequently, the ionized gas 30 containing no ozone is drawn into the refrigerator 38.

Hence, ion concentration in the refrigerator 38 increasingly becomes higher. The generating ion, however, is partially consumed by contacting a wall surface of the refrigerator 38, the cooler 9, and the like so that the ion concentration in the refrigerator 38 can be kept at substantially a constant value.

Therefore, the ion can continuously be supplied for the foods 8 housed in the refrigerator 38, resulting in reduction of the microbe propagation in the foods 8.

Appropriate ion concentration in the refrigerator 38 may vary depending upon a condition such as a kind of the food, a temperature or humidity in the refrigerator 38. Experimental results show that there is an effect of preventing the microbe propagation even in extremely low ion concentration which is about several times normal ion concentration in air (i.e., in the range of tens to about 100 ions/cm$^3$). However, preferable ion concentration is ten to a thousand times the normal ion concentration, that is, ion concentration in the range of $10^3$ to $10^5$ ions/cm$^3$ is highly effective, and is economical.

A description will now be given of the reduction of the microbe propagation by the ion with reference to an illustrative experiment.

FIG. 8 shows results of the illustrative experiment. In the illustrative experiment, slices of raw tuna were used as the foods 8. After the raw tuna has been preserved for three days in the refrigerator 8 at a temperature of 5° C. and at the humidity in the range of 80 to 95%, the raw tuna was continuously processed by the negative ion generated in the ozone decomposing chamber 28.

In this case, voltage in the range of 3 to 5 kV was applied between electrodes in the ionization chamber 23 so as to maintain the ion concentration in the refrigerator 8 in the range of about $10^3$ to $10^4$ ions/cm$^3$.

Advantages of the present invention will become more apparent in light of the following comparison between an effect in case of no processing and another effect in case of processing in which the foods 8 contacts the ozone rather than the ion.

Figure 30:
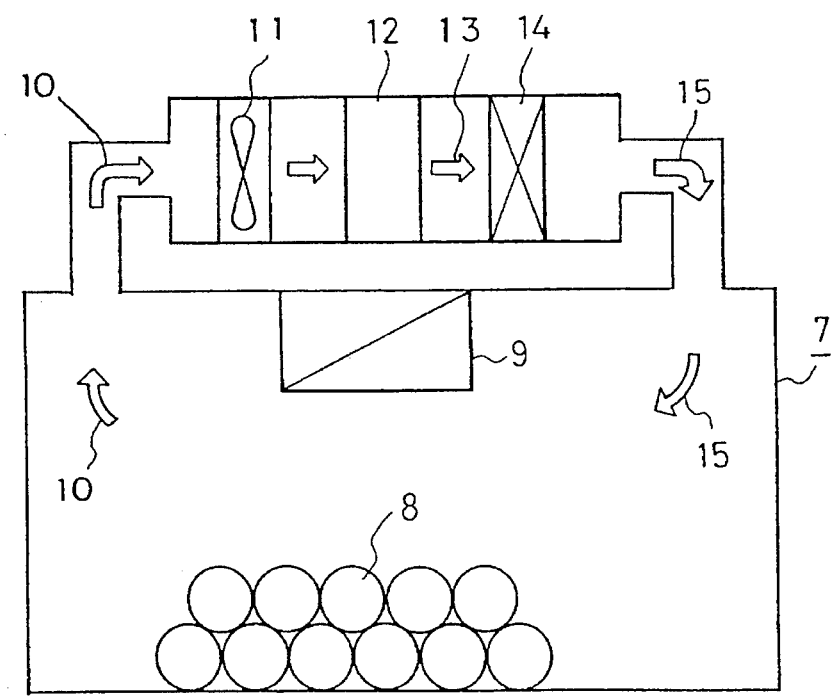
FIG. 30 is a diagram showing a configuration of the conventional microbe propagation preventing apparatus.

Ozone processing was performed without an ozone decomposing catalyst 14 shown in FIG. 30. In the processing, the ozone concentration in the refrigerator 38 was maintained at about 1.0 ppm, and five slices of raw tuna serving as samples were extracted for each processing from many slices at random. Sampling of general bacteria on a surface of the foods 8 was performed according to an impression method, and a standard agar medium was employed as a culture medium.

As a result of the experiment, in the no processing (i.e., in case supplying no ion and no ozone), the sliced raw tuna was tinged with black, freshness thereof was degraded, and there was generated putrid smell on the third day of the preservation as shown in FIG. 8. At this time, the number of general bacteria on the surface of the sliced raw tuna was multiplied to about 200/cm$^2$.

Further, when continuous processing was performed in an ion atmosphere having extremely low concentration of $10^4$ ions/cm$^3$, it has been possible to completely maintain the original freshness of the sliced raw tuna for three days. There was no putrid smell, and the viable cell number on the surface on the third day was about 20/cm$^2$ which was substantially the same number as viable cell number before starting the illustrative experiment.

In addition, when continuous processing was performed at the ozone concentration of about 1 ppm, there was no putrid smell like substantially the ion processing, and the viable cell number on the surface was substantially the same number as that in the ion processing. However, there were generated problems in that appearance of the sliced raw tuna discolored into dark-red due to a strong oxidative effect of the ozone, and quality was considerably degraded.

Subsequently, the ion processing was performed one to three times a day, and was intermittently performed for a period ranging from 5 to 30 minutes for each ion processing. In this case, an effect of preventing the microbe propagation was slightly degraded as compared with the above continuous processing, but the intermittent processing provided substantially the same effect. Even in the intermittent processing, higher ion concentration of about $10^5/cm^3$ enabled entirely the same microbe propagation preventing effect as that in the continuous processing.

On the other hand, when intermittent ozone processing was performed as in the intermittent ion processing, the microbe propagation preventing effect was significantly degraded as compared with the continuous processing, and the sliced raw tuna discolored into dark-red as in the continuous processing.

As is clear from the above facts, it is understood that the propagation of the microbe adhering the surface of the sliced raw tuna can be prevented without discoloration or degeneration of the sliced raw tuna unlike the ozone processing, and the original freshness can be maintained according to the extremely low concentration ion processing using the ion which is generated by gaseous discharge or ionization.

In this connection, if gaseous oxygen is supplied for the ionization chamber 23 as the gas 1 instead of the air, a generation efficiency of the ion can be enhanced since oxygen concentration in the gas becomes about five times higher than that in case the air is employed.

Though the embodiment 10 has been discussed with reference to a case of the processing using the negative ion, the positive ion can provide the same effect. The negative ion, however, has a more excellent effect of preventing the propagation of the microbe than that of the positive ion.

Referring now to FIG. 9, there is shown an effect of the ion processing in which bacteria (*Pseudomonas aeruginosa* of the Pseudomonas genus which was a microbe obtained from dust adhering a fan of an air-conditioner) were artificially planted in the agar-medium instead of the foods 8 in a Petri dish, and the Petri dish holding the bacteria was mounted in the refrigerator 38. In this case, the Petri dish was mounted in the refrigerator 38 at an atmosphere having ion concentration in the range of $10^3$ to $10^4$ ions/$cm^3$, and at a temperature of 25° C. and at humidity ranging from 50 to 70%. The Petri dish has been in a still standing condition for three days under the above conditions, and the standard agar medium was employed as the culture medium. Further, voltage in the range of 3 to 5 kV was applied between the electrodes in the ionization chamber 23 so as to generate the negative ion.

As shown in FIG. 9, in case of no processing, a bacteria colony was multiplied to about 370 colonies for each Petri dish on the third day while, in case of the ion processing, multiplication of the bacteria colony could considerably be reduced to about 14 colonies for each Petri dish on the third day. Further, in case of the ozone processing having concentration of 0.01 ppm (i.e., about $3\times10^{11}$ ozone/$cm^3$) which is about $10^7$ times higher than the ion concentration, there was no effect of preventing propagation of the bacteria. Finally, the bacteria colony was multiplied to about 350 colonies for each Petri dish on the third day like substantially the no processing.

As set forth above, the propagation of the bacteria planted in the agar medium can also be prevented by the extremely low concentration ion processing. Further, it can be assumed from the above experimental results that ion ability of preventing the microbe propagation is about $10^7$ times higher than ozone ability.

FIG. 9 shows only the effect of the negative ion by using the bacteria of the Pseudomonas genus. However, the same effect can be provided by other bacteria such as *coli* bacteria, or salmonella.

FIG. 10 shows an ion processing effect on mold (fungus) adhering a strawberry. In this experiment, there were provided an ion processing section (at an atmosphere having concentration ranging from $10^3$ to $10^4$ ions/$cm^3$), a no processing section, and an ozone processing section (at an atmosphere having concentration of about 0.01 ppm) in the refrigerator 38. Further, a temperature was set at 7° C., and the humidity was set in the range of 80 to 95%, and the strawberry has been preserved for seven days under the previous environmental conditions. The fungus (the mold) adhering a surface of the strawberry was obtained according to the impression method on the eighth day, and was transplanted to a mold culture medium so as to be cultured. In this case, there is a problem in that the strawberry changed from red to white when the ozone concentration was increased to 0.01 ppm or more.

As a result of the experiment, the number of fungi was reduced by the ion processing to about one-tenth of that in case of the no processing or the ozone processing. It is thus possible to prevent the microbe propagation of the fungi (the mold) by the extremely low concentration ion processing.

Embodiment 11

Figure 11:
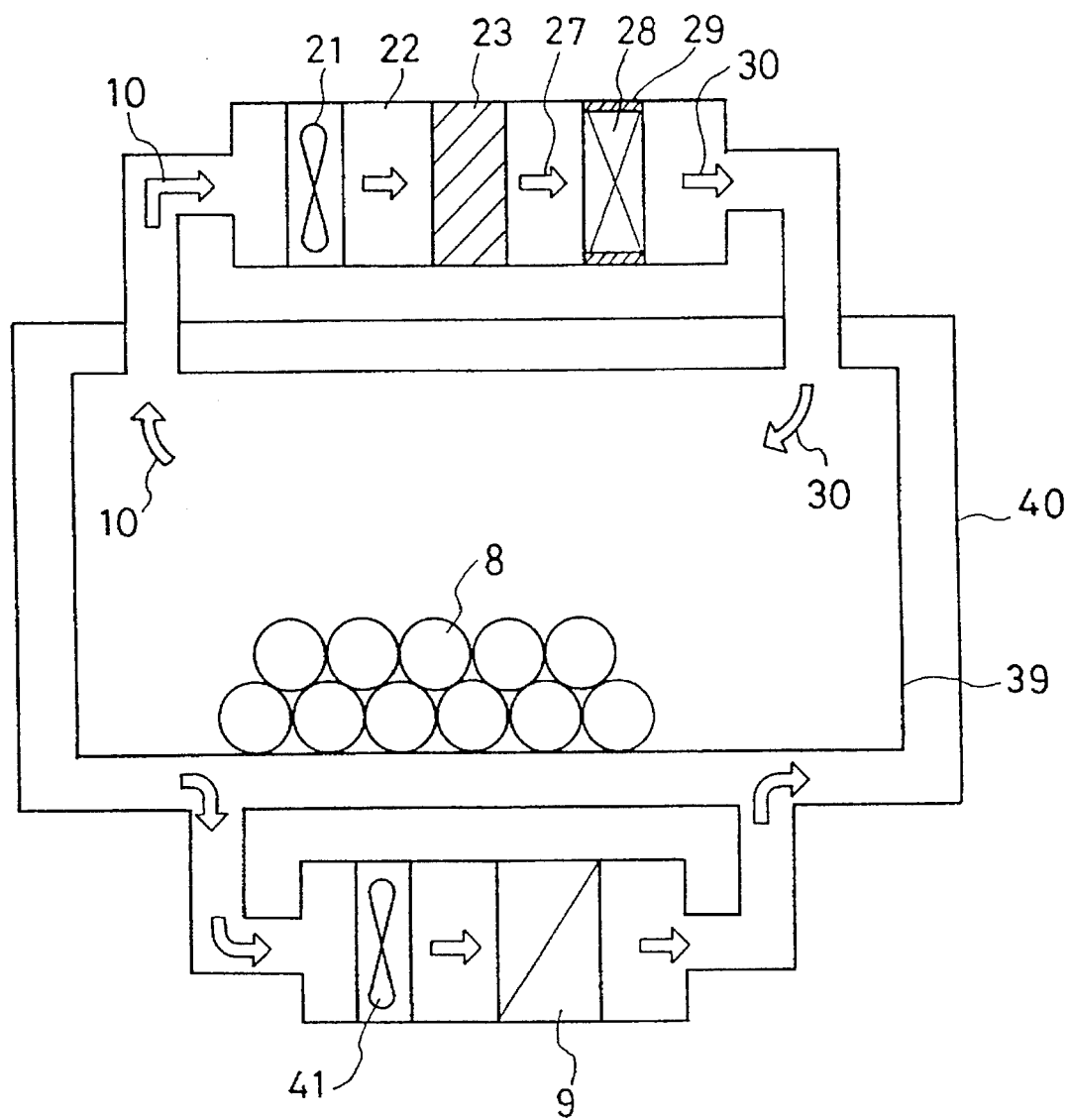
FIG. 11 is a diagram showing a configuration of a microbe propagation preventing apparatus according to the embodiment 11 of the present invention.

The embodiment 10 has been described with reference to a case where a gas 10 in a refrigerator 39 does not circulate through an ionization chamber 23, or an ozone decomposing chamber 28, but circulates in the refrigerator 39. However, as shown in FIG. 11, the gas 10 in the refrigerator 39 may be circulated through the ionization chamber 23, or the ozone decomposing chamber 28.

In this case, since the gas 10 in the refrigerator 39 passes through the ozone decomposing chamber 28, it is possible to provide another effect of deodorizing an odor of the gas 10 in addition to the effect in the embodiment 10.

The amount of ion, however, is reduced by passing through the ozone decomposing chamber 28 as compared with the embodiment 10. Hence, in order to minimize the reduction of the ion, a cooler 9 is provided externally to a refrigerator 39 (an ion supplying portion) so that the cold from the cooler 9 is circulated by a fan 41 through a circulation duct 40, and the gas 10 is cooled through the circulation duct 40.

Alternatively, as shown in FIGS. 12 and 13, the ionization chamber 23 or the ozone decomposing chamber 28 may be provided in the refrigerator 39, resulting in the same effect.

Embodiment 12

In the embodiments, ac voltage is applied between electrodes in an ionization chamber 23. However, negative dc voltage may be applied instead of the ac voltage. Alternatively, negative dc pulse voltage may be applied at an interval of tens microseconds.

It is thereby possible to selectively obtain a negative ion.

Embodiment 13

In the above embodiments 10 and 11, there is no restriction on a material of an inner surface of a refrigerator 38 or 39. However, if the refrigerator 38 or 39 is provided with the inner surface made of an insulating material, it is possible to prevent reduction of ions in the refrigerator 38 or 39.

Embodiment 14

Figure 14:
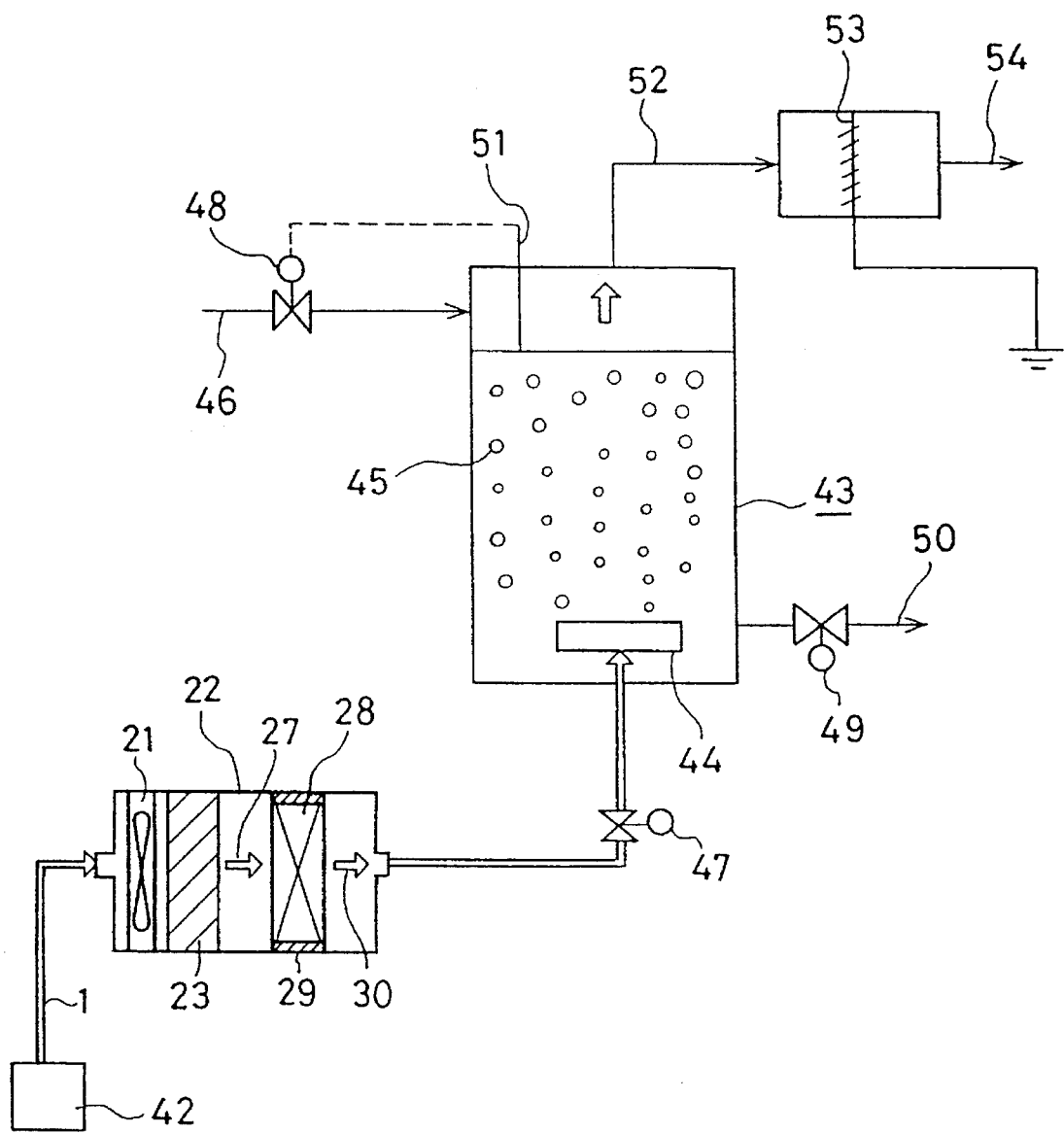
FIG. 14 is a diagram showing a configuration of a microbe propagation preventing apparatus according to the embodiment 14 of the present invention.

FIG. 14 is a diagram showing a configuration of a microbe propagation preventing apparatus according to the embodiment 14 of the present invention. In FIG. 14, reference numeral 42 means a gas supplying apparatus such as a compressor for supplying air or oxygen, 43 means a water reservoir storing liquid in which microbes can be propagated, 44 is a diffuser (a diffusing apparatus) to transform an ionic gas from which ozone is removed by an ozone decomposing chamber 28 into bubbles so as to provide the bubbles into water of the water reservoir, 45 is a bubble, 46 is water to be processed, 47, 48 and 49 are solenoid valves, 50 is processed water which is processed by an ionized gas 30, 51 is a level sensor to measure a water level, 52 is an ionized gas containing an excess ion, 53 is a mesh-like metallic net to remove the excess ion, and 54 is a processed gas from which the excess ion is removed.

A description will now be given of the operation.

First, the solenoid valve 48 is opened to feed the water to be processed 46 into the water reservoir 43, and the water to be processed 46 is stored in the water reservoir 43. Subsequently, the gas supplying apparatus 42 is operated, and the solenoid valve 47 is concurrently opened to generate the ionized gas 30 from the ozone decomposing chamber 28 as in the embodiment 1.

The ionized gas 30 is fed to diffuser 44 made of ceramic or the like, and is diffused into the water reservoir 43 as the fine bubbles 45. Thereby, the water to be processed in the water reservoir 43 can contact the ionic fine bubble 45 containing the ion so that the propagation of the microbe such as bacteria can be prevented. The water in the water reservoir 43 may be used as potable water or used as the processed water 50 as desired when the solenoid valve 49 is opened.

When the water level is lowered by using the processed water in the water reservoir 43, a signal is outputted from the level sensor 51 to open the solenoid valve 48 so as to feed the water to be processed 46 into the water reservoir 43 again. On the other hand, the excess ionized gas 52 is introduced into the mesh-like metallic net 53 which is grounded, and is discharged as the processed gas 54 after excess ion is removed from the gas 52.

In case the processed water 50 from the water reservoir 43 is intermittently used, the gas-liquid mixer 42 is intermittently operated according to the intermittent usage. On the other hand, in case the processed water 50 is continuously used, the water to be processed 46 is continuously supplied so that the microbe propagation preventing apparatus according to the embodiment 14 is continuously operated. In this connection, though it is preferable that ion concentration of the ionized gas 30 is as high as possible, only a little amount of ion may be injected into the water to be processed 46 because ion ability of preventing the microbe propagation is about $10^7$ times higher than ozone ability as shown in the experimental results in FIGS. 9 and 10. Further, a flow rate of the ionized gas 30 supplied into the water reservoir 43 is preferably adjusted such that the ionized gas 30 can be injected into the water reservoir 43 with a residence time ranging from several to about tens minutes in the water reservoir 43.

Though the compressor is employed as the gas supplying apparatus 42 in the embodiment 14, a generation efficiency of the ion may be enhanced by supplying gaseous oxygen by using a steel cylinder of the gaseous oxygen, or lox. Further, the ozone decomposing chamber 28 may be removed since the ozone can be decomposed in the water for a time period less than several minutes.

Embodiment 15

Figure 15:
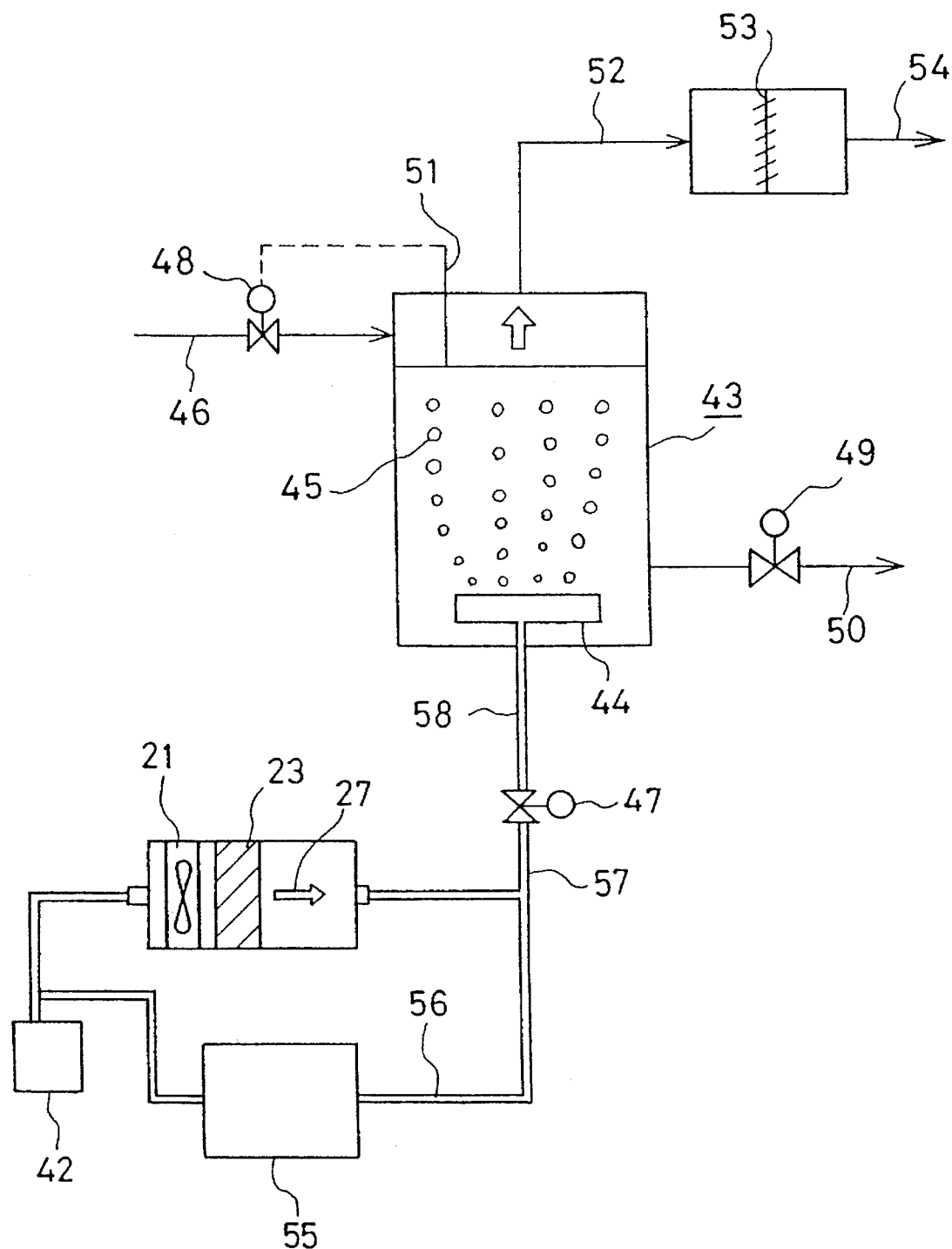
FIG. 15 is a diagram showing a configuration of a microbe propagation preventing apparatus according to the embodiment 15 of the present invention.

Though only an ionized gas 30 is supplied to a diffuser 44 in the embodiment 14, as shown in FIG. 15, an ozonizer 55 may be provided to generate ozone, and a pipe (a gas mixer) 57 may be provided to mix an ionized gas 27 with an ozonized gas 56 so as to supply a mixed gas 58 to the diffuser 44.

In this case, it is possible to provide a synergistic effect of the ion and the ozone so as to more surely reduce propagation of microbes, and sterilize the microbes.

Embodiment 16

Figure 16:
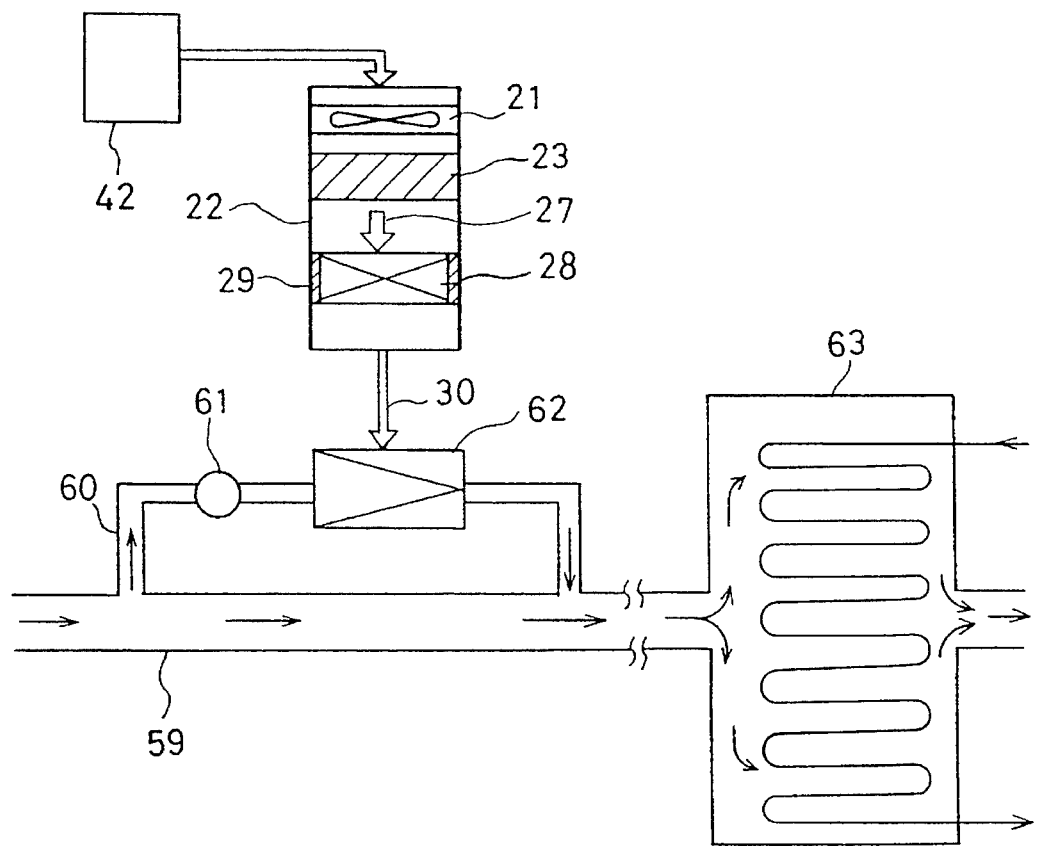
FIG. 16 is a diagram showing a configuration of a microbe propagation preventing apparatus according to the embodiment 16 of the present invention.

FIG. 16 is a diagram showing a configuration of a microbe propagation preventing apparatus according to the embodiment 16 of the present invention. In FIG. 16, reference numeral 59 means a water pipe through which plain water or sea water serving as cooling water passes, 60 means a branch pipe through which the cooling water partially flows from the water pipe 59, 61 is a pump, 62 is an ejector (a gas-liquid mixer) to mix an ionized gas 30 with the cooling water and dissolve the ionized gas 30 in the cooling water, and 63 is a heat exchanger in which hot water flows.

The plain water or the sea water serving as the cooling water passes through the water pipe 59 to be introduced into the heat exchanger 63, and is cooled the hot water flowing in the heat exchanger 63. In this case, there is generated slime on an inner wall or a surface of the water pipe 59 or the heat exchanger 63 due to propagation of microbes adhering the inner wall or the surface. Thus, flow pressure in the water pipe 59 increases, and a flow rate of the cooling water decreases. Further, the slime adhering the surface of the heat exchanger 63 considerably decreases a heat exchanging efficiency.

Hence, the pump 61 is operated to feed the partial cooling water flowing through the water pipe 59 to the ejector 62 so that the ionized gas 30 generated from an ozone decomposing chamber 28 is transformed into fine bubbles in the cooling water, and is dissolved in and mixed with the cooling water. The cooling water in which the ionized gas 30 is dissolved is mixed with the cooling water flowing through the water pipe 59, and is transferred to the heat exchanger 63 through the water pipe 59. At this time, it is possible to prevent the slime from adhering the inner wall of the water pipe 59 or the surface of the heat exchanger 63 because of a microbe propagation preventing effect inherent in the ionized gas 30.

In this case, there is an advantage in that, unlike the ozone, no corrosion of the water pipe 59 and the heat exchanger 63 occurs even if ion concentration of the ionized gas 30 is increased. In a conventional apparatus, in case the sea water is used as the cooling water, an ozonized gas is injected into the sea water to react with a bromine ion in the sea water so as to generate an oxidant such as hypobromous acid. Hence, an apparatus for removing the oxidant is conventionally required. However, there is an excellent advantage in that no oxidant is generated in case the ionized gas 30 is injected. Only a little amount of ion may be injected into the cooling water because ion ability of preventing the microbe propagation is about $10^7$ times higher than ozone ability as shown in the experimental results in FIGS. 9 and 10. In this connection, while an injection rate of the ionized gas 30 by ejector 62 may vary according to, for example, water quality or a temperature of the cooling water, it is possible to prevent adhesion of the slime by intermittently injecting the ionized gas 30 several times a day, for a period ranging from 5 to 30 minutes for each injection.

Embodiment 17

Though the embodiment 16 has been described with reference to a case of employing an ozone decomposing chamber 28, the ozone decomposing chamber 28 may be removed in case plain water is used as cooling water, or a little amount of ozone is generated in an ionization chamber 23. Further, in case the plain water such as river water or sewage is used as the cooling water, a mixed gas of an ion and ozone may be supplied into an ejector 62 as in the embodiment 15.

In this case, it is possible to provide a synergistic effect of the ion and the ozone so as to more surely reduce microbe propagation.

Embodiment 18

Figure 17:
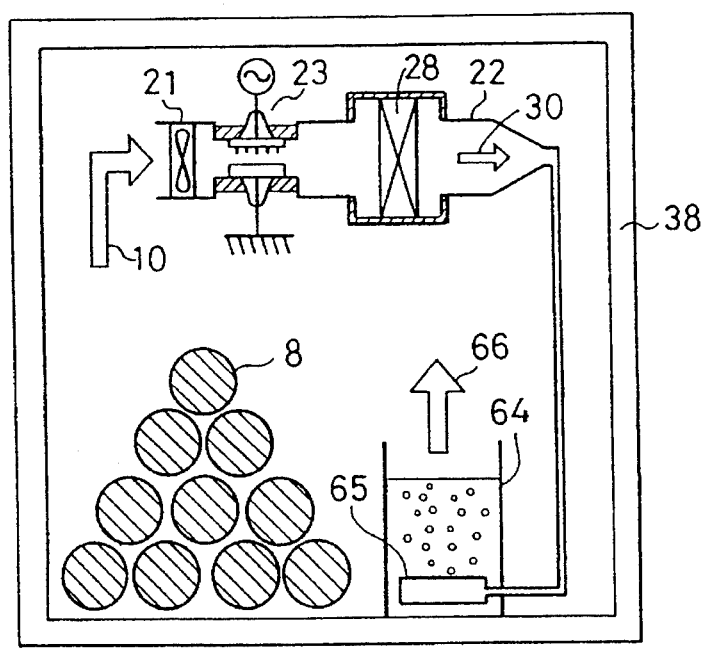
FIG. 17 is a diagram showing a configuration of a microbe propagation preventing apparatus according to the embodiment 18 of the present invention.
Figure 18:
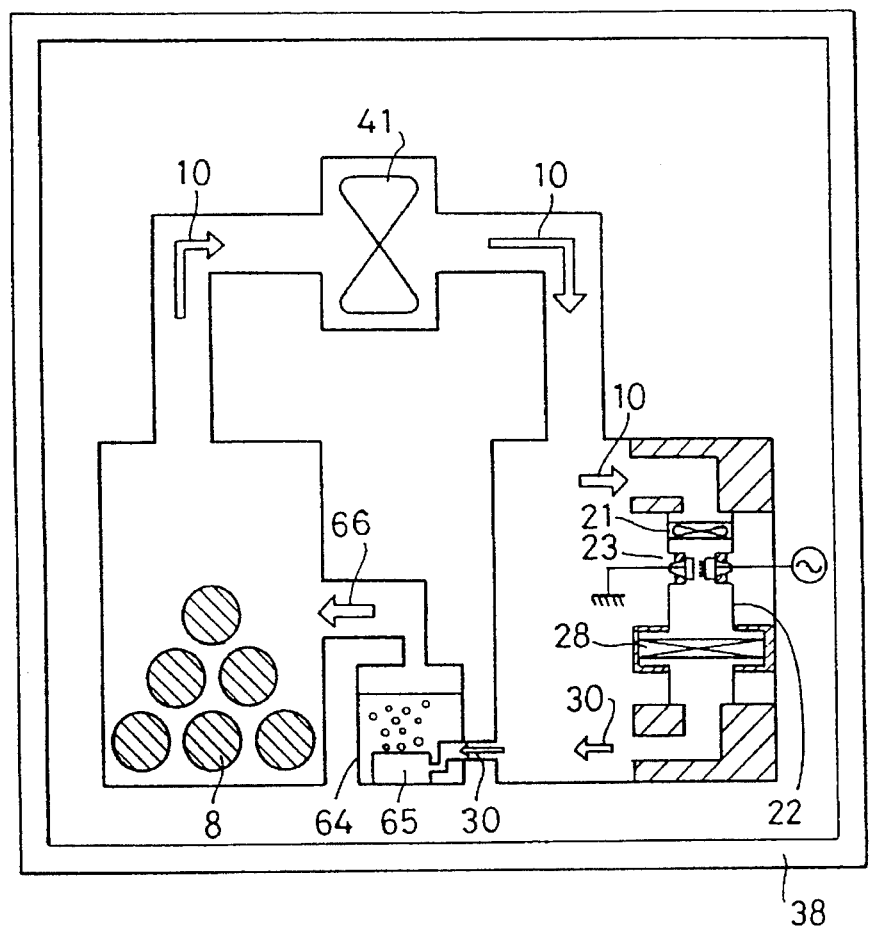
FIG. 18 is a diagram showing a configuration of the microbe propagation preventing apparatus according to the embodiment 18 of the present invention.

In the embodiments, an ionized gas 30 is directly supplied for foods 8. However, as shown in FIGS. 17 and 18, the gas 30 generated from an ozone decomposing chamber 28 may be diffused into a water tank 64 through, for example, a diffusing pipe 65 made of glass, and may be supplied for the foods 8 after the gas 30 is humidified.

In this case, desiccation of the foods 8 can be avoided, resulting in an enhanced preservation effect of the foods.

Embodiment 19

Figure 19:
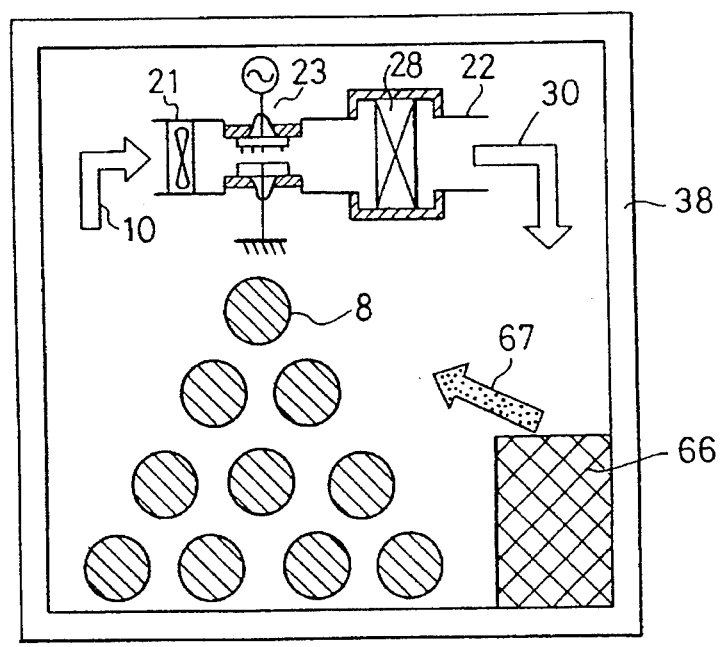
FIG. 19 as a diagram showing a configuration of a microbe propagation preventing apparatus according to the embodiment 19 of the present invention.
Figure 20:
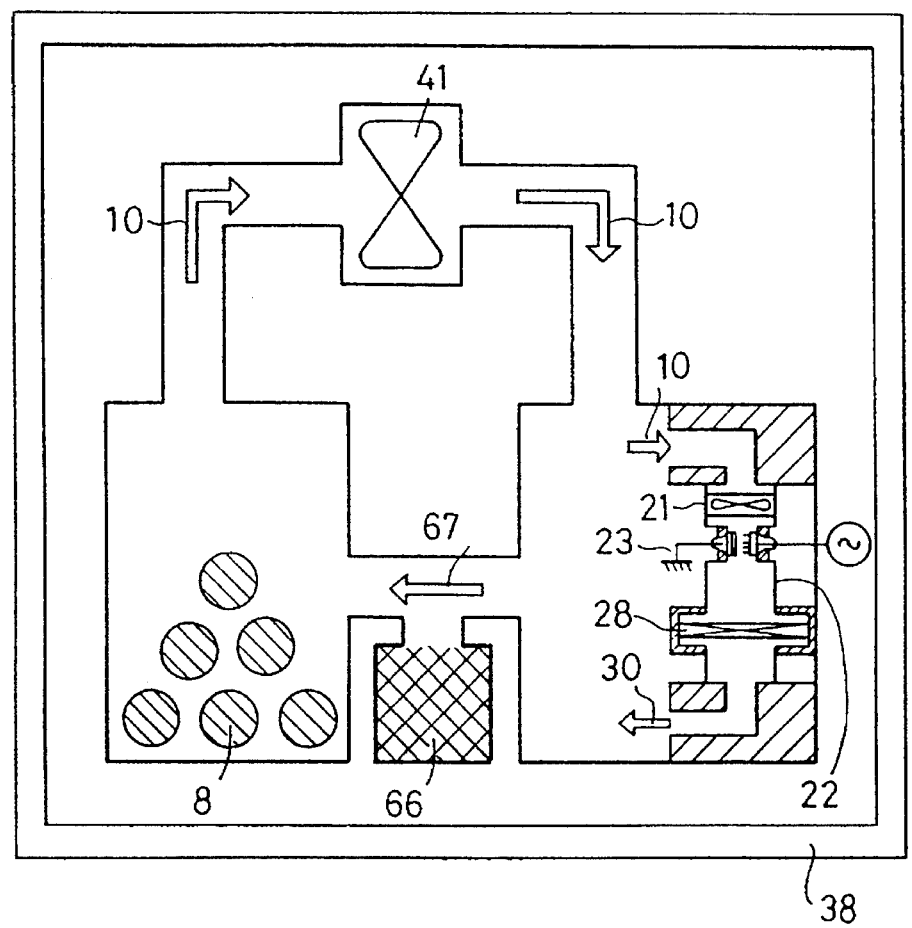
FIG. 20 is a diagram showing a configuration of the microbe propagation preventing apparatus according to the embodiment 19 of the present invention.

Though a gas 30 is humidified by using a water tank 64 in the embodiment 18, as shown in FIGS. 19 and 20, a humidifier may be mounted in a refrigerator 38 to humidify an atmosphere in the refrigerator 38, resulting in the same effect.

Embodiment 20

Figure 21:
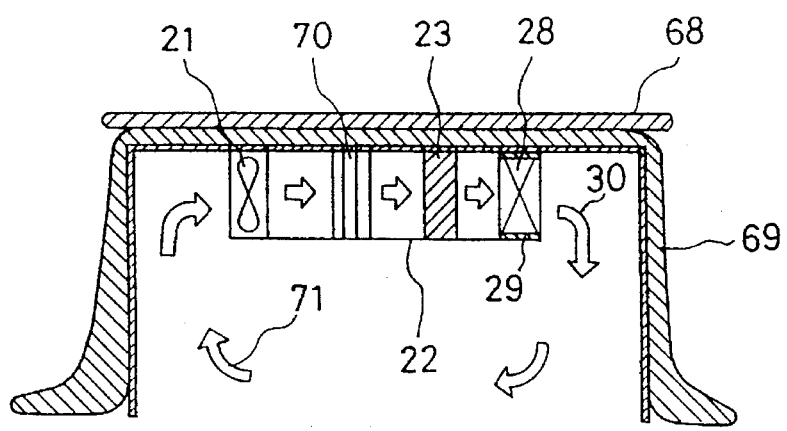
FIG. 21 is an explanatory view illustrating a microbe propagation preventing method according to the embodiment 20 of the present invention.

FIG. 21 is an explanatory view illustrating a microbe propagation preventing method according to the embodiment 20 of the present invention. In FIG. 21, reference numeral 68 means a foot warmer (a kotatsu), and 69 means a coverlet. The foot warmer 68 and the coverlet 69 form a closed space.

Further, reference numeral 70 means a heater for the foot warmer 68, and 71 means a gas in the closed space.

A description will now be given of the operation.

An atmosphere in the foot warmer 68 is substantially closed by the coverlet 69 for heating. In this condition, a fan 21 is operated so that the air 71 in the foot warmer is sucked by the fan 21 to be fed into the heater 70, resulting in an increased temperature.

Thereafter, the air 71 having the increased temperature is fed into an ionization chamber 23 and an ozone decomposing chamber 28 to become an ionized gas 30 containing no ozone as in the embodiment 1.

In this connection, since the ozone decomposing chamber 28 generates active oxygen at a time of decomposing the ozone, a malodorous organic substance can be removed from the air 71.

It is thereby possible to supply human skin with the ionized gas 30 containing no ozone which is harmful for a human body. Therefore, while variations may be caused according to conditions such as temperature and humidity, or a user's constitution, the ionized gas 30 can prevent the microbe propagation on the skin so that, for example, an effect of preventing athlete's foot or the like can be provided. In this embodiment, it is possible to provide a substantially efficient effect with ion concentration equivalent to the ion concentration which is generated in the respective embodiments.

The heat 70 is provided on the upstream side of the ionization chamber 23 in order to prevent the ion generated in the ionization chamber 23 from being consumed by the heater 70.

Embodiment 21

Figure 22:
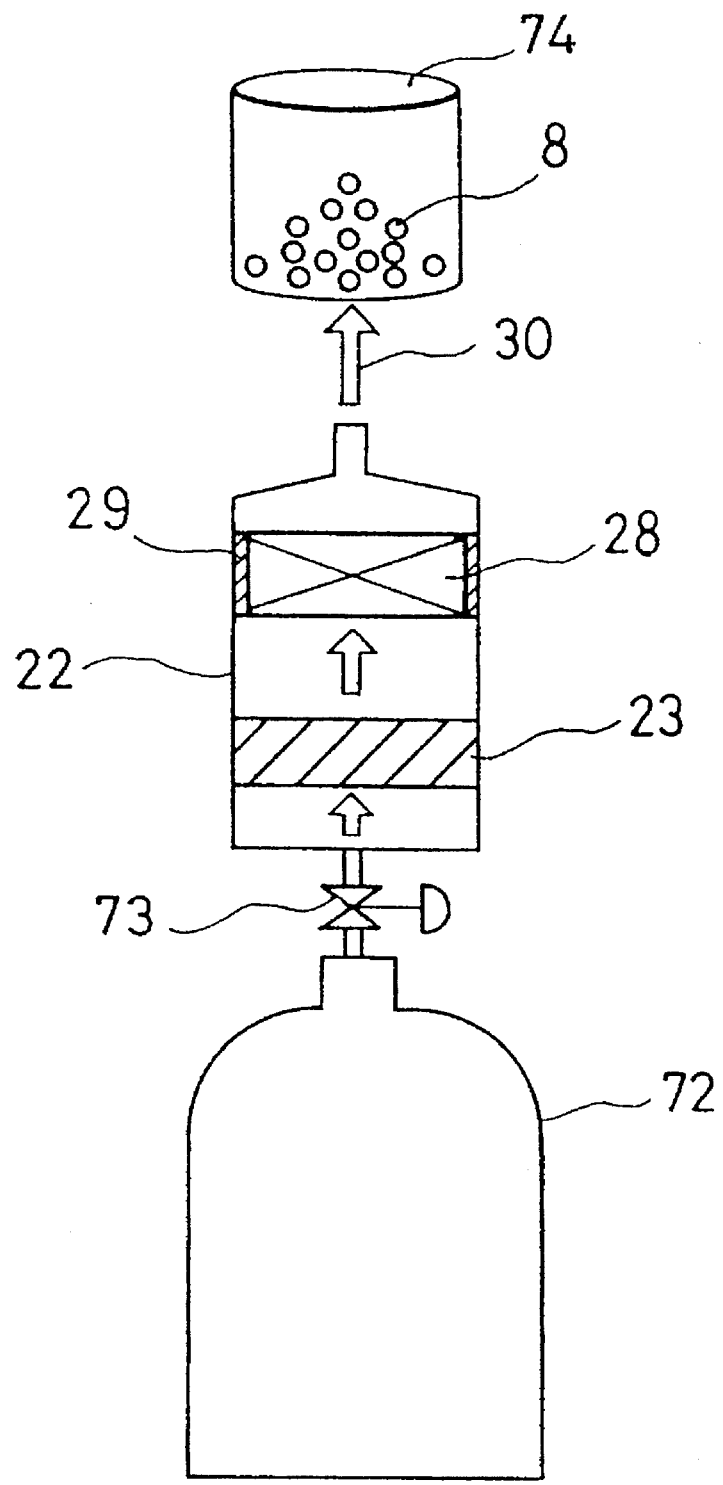
FIG. 22 is an explanatory view illustrating a microbe propagation preventing method according to the embodiment 21 of the present invention.

Though the embodiment 20 has been described with reference to a foot warmer serving as a closed space, a negative ion may be injected into a preservation sack 74 made of, for example, polyethylene in which foods 8 is sealed as shown in FIG. 22.

In this case, it is possible to prevent microbe propagation in the foods sealed in the preservation sack 74. Reference numeral 72 means air or an oxygen supplying apparatus (for example, a bomb), and 73 is a solenoid valve.

Embodiment 22

Figure 23:
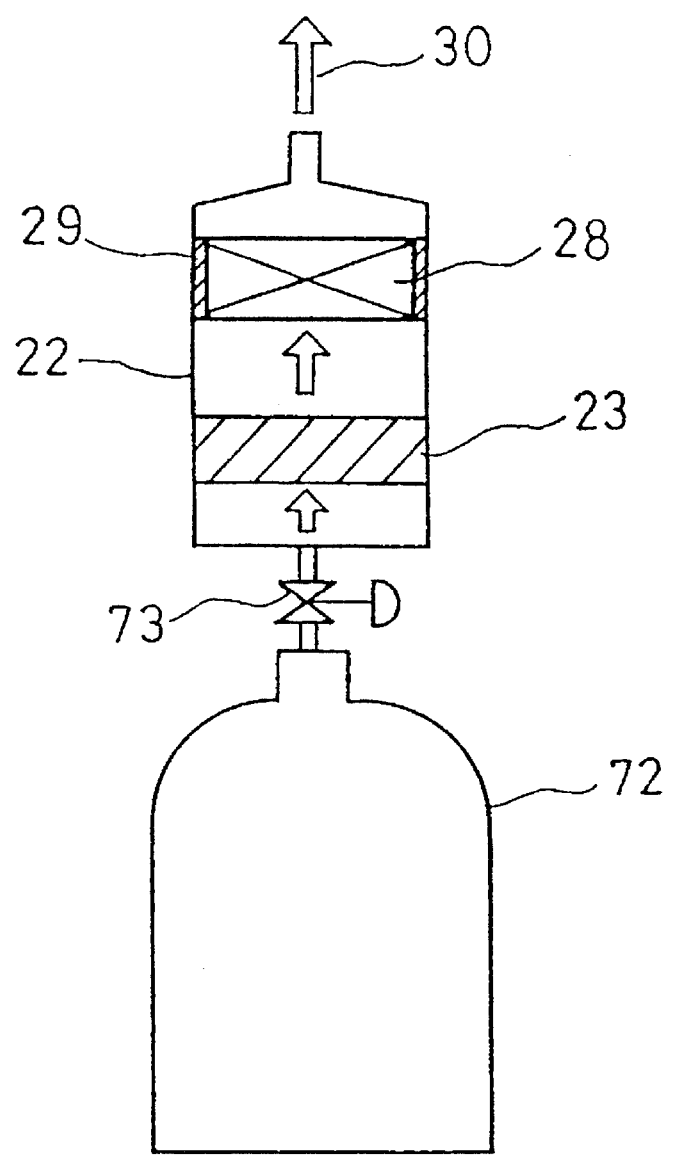
FIG. 23 is an explanatory view illustrating a microbe propagation preventing method according to the embodiment 22 of the present invention.

Though an ionized gas 30 is supplied to a closed space in the embodiments 20 and 21, as shown in FIG. 23, the ionized gas 30 may be supplied into air.

It is thereby possible to directly supply the ionized gas 30 to, for example, a carious tooth, or a dermatitis part which is caused due to microbes such as bacteria, resulting in an effect of prevention or medical treatment of the carious tooth and the dermatitis.

Embodiment 23

Figure 24:
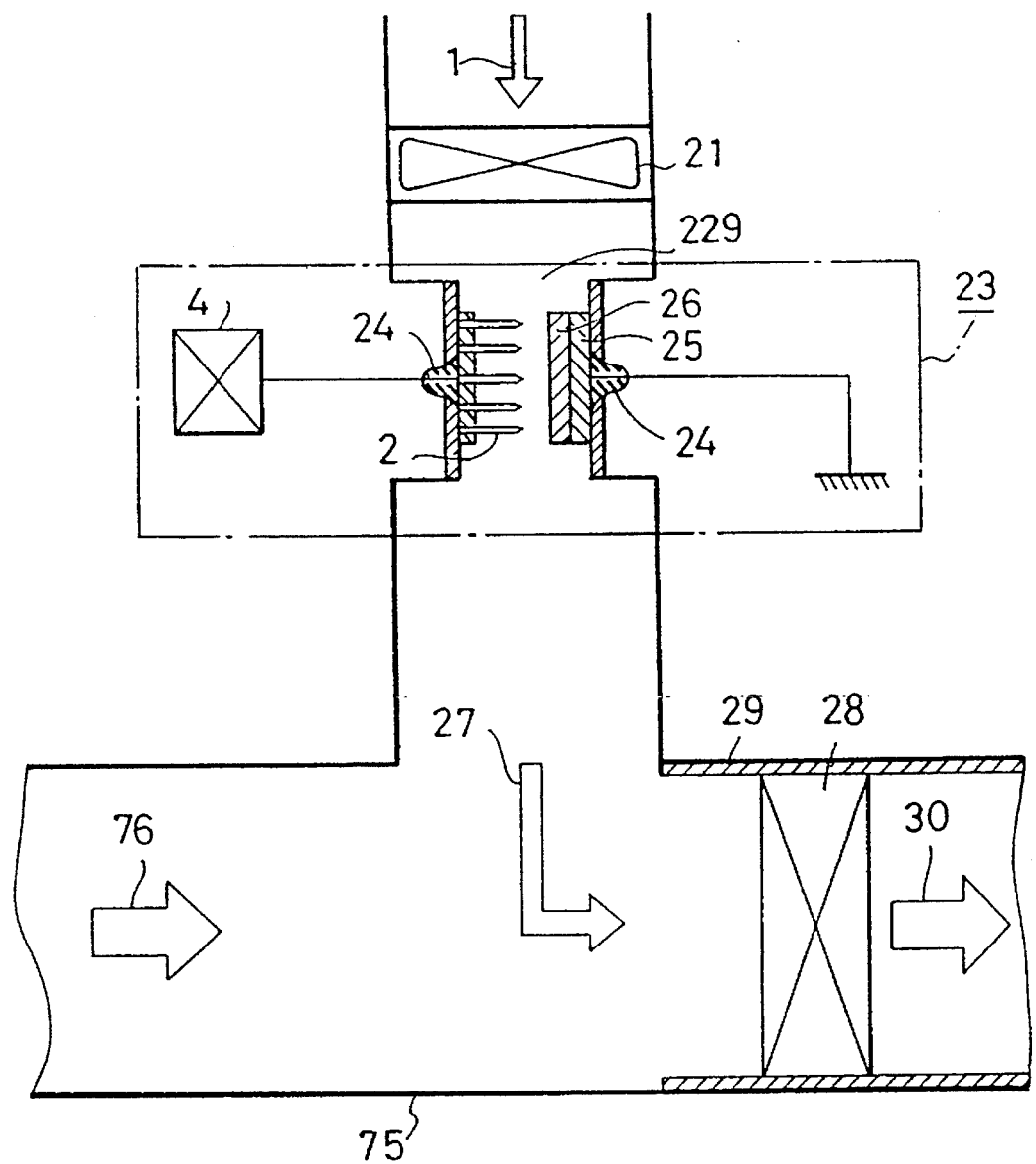
FIG. 24 is an explanatory view illustrating a microbe propagation preventing method according to the embodiment 23 of the present invention.

Though an ionized gas 30 is supplied into air in the embodiment 22, as shown in FIG. 24, the ionized gas 30 may be supplied to, for example, a gas to be processed 76 flowing in a duct 75 of an air cleaning apparatus. Consequently, it is possible to remove microbes such as bacteria or mold which can be propagated in the duct 75, and provide a comfortable space for human.

Embodiment 24

Figure 25:
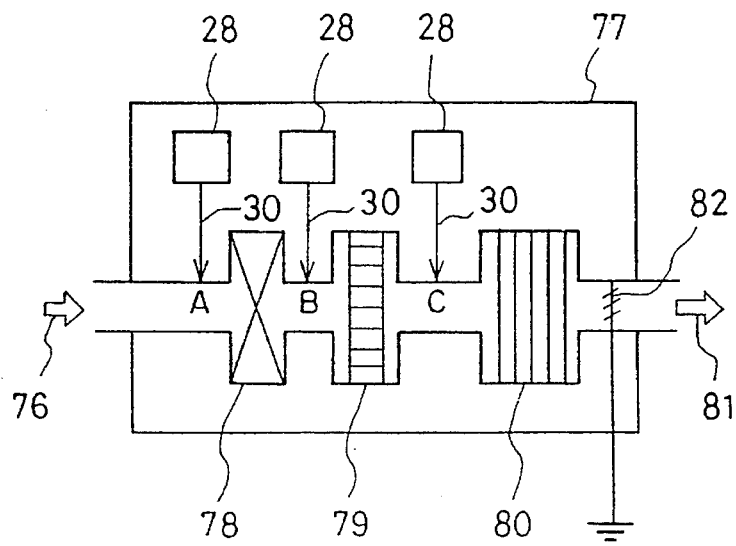
FIG. 25 is an explanatory view illustrating a microbe propagation preventing method according to the embodiment 24 of the present invention.

FIG. 25 is an explanatory view illustrating a microbe propagation preventing method according to the embodiment 24 of the present invention. In FIG. 25, reference numeral 77 means an air-conditioning system such as an air-conditioner or an air cleaning apparatus, 78 means a filter to remove dust contained in a gas to be processed 76, 79 is a wind blower such as a scirocco fan, 80 is a heat exchanger in a heat pump mode, 81 is an air-conditioned gas, and 82 is a mesh-like metallic net (a conductive net) to remove an excess ion. In FIG. 25, marks A, B, and C denote points for injecting the ion, and an ionization chamber 23 and the like are omitted for the sake of simplicity in the drawing.

A description will now be given of the operation.

The air-conditioning system such as air-conditioner is mounted in an unillustrated room. The wind blower 79 is operated so that the gas to be processed 76 serving as air in the room passes through the filter 78, and the wind blower 79 in this order, and is thereafter introduced into the heat exchanger 80. The gas to be processed 76 is cooled or heated in the heat exchanger 80, and is returned into the room as the air-conditioned gas 81.

As shown in FIG. 25, the ion is injected into the gas to be processed 76 at the ion injecting points A, B, and C in the air-conditioning system 77.

Accordingly, the gas to be processed 76 contains the ion so that the gas to be processed 76 can prevent the microbe propagation such as adhesive bacteria adhering surfaces of the filter 78, the wind blower 79, and the heat exchanger 80 while passing therethrough. Thereby, no dust adheres the surfaces of the filter 78, the wind blower 79, and the heat exchanger 80.

The excess ion in the gas to be processed 76 can be removed by the mesh-like metallic net 82.

In this connection, though variations may be caused according to a condition such as a kind of the microbe, a temperature, the humidity, or the wind velocity, a period of the microbe propagation is typically in the range of several hours to several days. Hence, the ion may be intermittently supplied to the gas to be processed 76 for a short time approximately multiple minutes every two to three hours or every half a day. In this case, the ion is preferably injected such that ion concentration in the gas to be processed 76 is in the range of $10^2$ to $10^5$ ions/cm$^3$.

Though the ionized gas 30 is supplied at the three points A, B, and C in the embodiment 24, the ionized gas 30 may be supplied at any two points or any one point in the three points A, B, and C as desired.

In the embodiment 24, the invention is applied to prevent the propagation of the adhesive bacteria due to adhesion of the dust to the heat exchanger 80 in the air-conditioning system 77 such as air-conditioner under a normal temperature condition. However, it is naturally possible to prevent the propagation of the microbes adhering the surface of the heat exchanger in a refrigerator under a low temperature condition. It is thereby possible to further widely reduce the adhesion of the dust or moisture condensation (the moisture condensation being caused due to the microbe to serve as a frosting core in the frosting of the heat exchanger) on the surface of the heat exchanger.

Further, the ionized gas 30 is supplied to the heat exchanger 80 mounted inside the air-conditioning system 77 in the embodiment 24. However, it is to be understood that the heat exchanger may be mounted externally to the air-conditioning system 77 and mounted outside the room so as to prevent the dust from adhering the heat exchanger.

Embodiment 25

Figure 26:
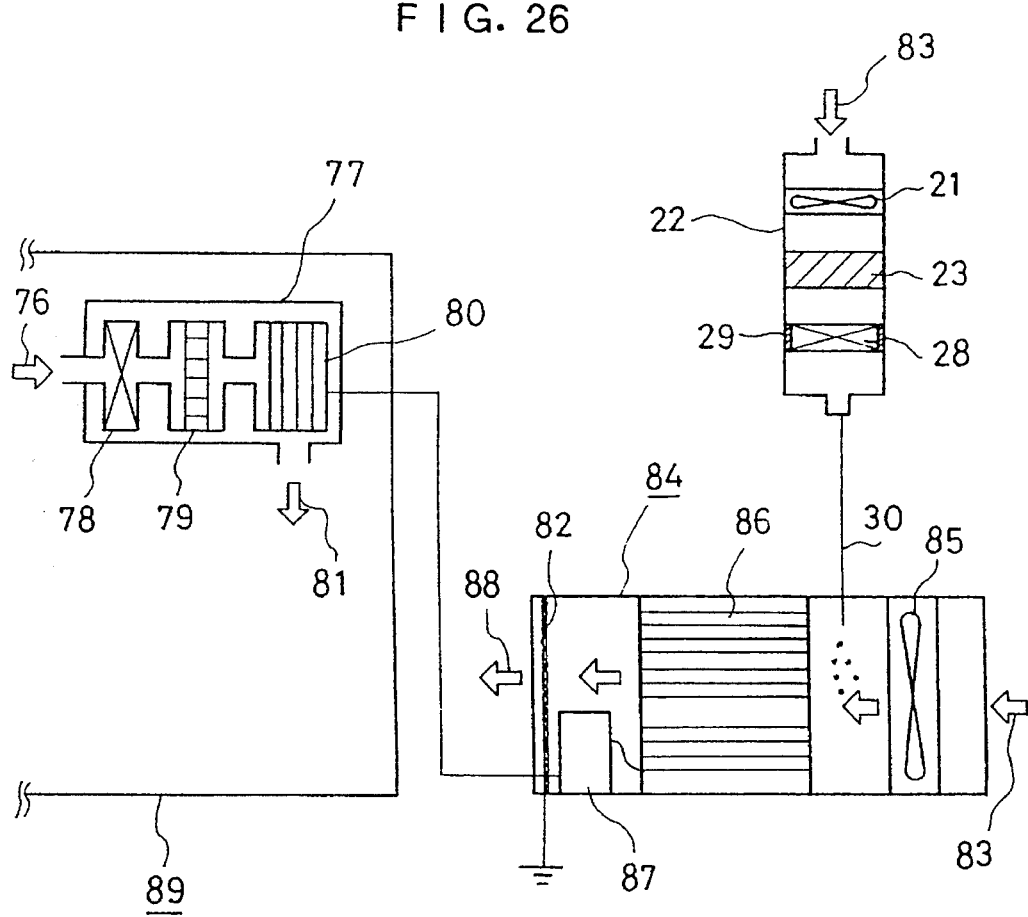
FIG. 26 is an explanatory view illustrating a microbe propagation preventing method according to the embodiment 25 of the present invention.

FIG. 26 is an explanatory view illustrating a microbe propagation preventing method according to the embodiment 25 of the present invention. In FIG. 26, reference numeral 83 means external air, 84 means an outdoor heat exchanging apparatus, 85 is a fan, 86 is a heat exchanger, 87 is a compressor for compressing a cooling medium, 88 is a gas discharged into the atmosphere, and 89 is a room.

A description will now be given of the operation.

In the outdoor heat exchanging apparatus 84, the fan 85 is operated so that the external air 83 is sucked by the outdoor heat exchanging apparatus 84 to be fed into the heat exchanger 86. In this case, the heat exchanger 86 discharges heat required for liquefying or vaporizing the cooling medium into the external air 83, otherwise, heat is drained from the external air 83.

In this condition, an ionized gas 30 is intermittently injected, for example, between the fan 85 and the heat exchanger 86 at approximate intervals ranging from 5 to 10 minutes, and is introduced into the heat exchanger 86. As a result, no adhesive bacteria, no dust adhere the surface of the heat exchanger 86 so that reduction of a heat exchanging efficiency can be prevented. An excess ion in the external air 83 can completely be removed by the mesh-like metallic net 82 which is grounded, resulting in no excess ion contained in the gas discharged into the atmosphere 88.

Embodiment 26

Figure 27:
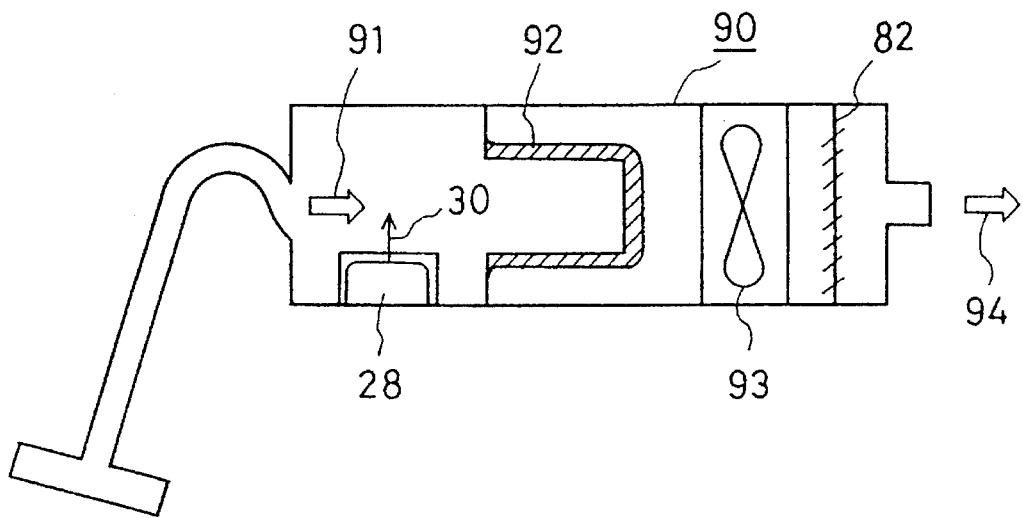
FIG. 27 as an explanatory view illustrating a microbe propagation preventing method according to the embodiment 26 of the present invention.

FIG. 27 is an explanatory view illustrating a microbe propagation preventing method according to the embodiment 26 of the present invention. In FIG. 27, reference numeral 90 means a cleaning machine, 91 means a gas to be processed containing dust, refuse, and the like, 92 is a filter to remove the dust and the refuse, 93 is a fan, and 94 is an exhausted gas.

A description will now be given of the operation.

The cleaning machine 90 is started to operate the fan 93 so that the contaminated gas to be processed 91 containing the dust and the refuse in the room is sucked into the cleaning machine 90 to pass through the filter 92, and is again exhausted into the room. In this case, since an ionized gas 30 is injected into the gas to be processed 91, the ionized gas 30 can prevent propagation of microbes adhering the filter 92. The microbe propagation in the gas 91 is prevented, and an excess ion in the gas 91 can completely be removed by the mesh-like metallic net 82.

As set forth above, according to the first aspect of the present invention, the ozone decomposing chamber is mounted to be electrically insulated from the air duct. As a result, there are effects in that reduction of the generating negative ion can be prevented in the ozone decomposing chamber, and the microbe propagation can be prevented.

According to the second aspect of the present invention, the air duct is made of the insulating material. As a result, there are effects in that reduction of the generating negative ion can be prevented in the ozone decomposing chamber, and the microbe propagation can be prevented.

According to the third aspect of the present invention, the ozone decomposing chamber includes the grid-like heating resistor which is coated with the insulating material. As a result, there are effects in that reduction of the generating negative ion can be prevented in the ozone decomposing chamber, and the microbe propagation can be prevented.

According to the fourth aspect of the present invention, the case body of the ozone decomposing chamber is made of the insulating material. As a result, there are effects in that reduction of the generating negative ion can be prevented in the ozone decomposing chamber, and the microbe propagation can be prevented.

According to the fifth aspect of the present invention, the air duct is surrounded by the heat insulating material. As a result, there are effects in that a decrease of the temperature of the ionized gas can be reduced so as to promote decomposition of the ozone.

According to the sixth aspect of the present invention, the moisture removing means for removing the moisture in the gas ionized by the ionization chamber is provided on the upstream side of the ionization chamber. As a result, there are effects in that an amount of the moisture in the gas can be reduced so as to promote generation of ions.

According to the seventh aspect of the present invention, the pair of conductive nets are disposed parallel to each other at the predetermined interval between the ionization chamber and the ozone decomposing chamber, the dc power source is provided to apply the positive dc voltage to one conductive net disposed on the downstream side in the pair of conductive nets, and the other conductive net disposed on the upstream side is grounded. As a result, there are effects in that only the negative ion can be obtained while the positive ion is removed, and a lifetime of the obtained ion can be extended.

According to the eighth aspect of the present invention, the pair of conductive nets are disposed parallel to each other at the predetermined interval between the ionization chamber and the ozone decomposing chamber, the dc power source is provided to apply the negative dc voltage to one conductive net disposed on the downstream side in the pair of conductive nets, and the other conductive net disposed on the upstream side is grounded. As a result, there are effects in that only the positive ion can be obtained while the negative ion is removed, and a lifetime of the obtained ion can be extended.

According to the ninth aspect of the present invention, one conductive net disposed on the downstream side has a coarser mesh than that of the other conductive net disposed on the upstream side in the pair of conductive nets. As a result, there is an effect in that a decrease of the obtained ion can be prevented.

According to the tenth aspect of the present invention, the ionic gas from which the ozone is removed by the ozone decomposing chamber is supplied into the space housing the object in which the microbes can be propagated. As a result, there is an effect in that the microbe propagation in the object can be prevented without damage to the object.

According to the eleventh aspect of the present invention, the ionic gas from which the ozone is removed by the ozone decomposing chamber is supplied into the space housing the object in which the microbes can be propagated, and the gas supplied into the space is returned to the ionization chamber. As a result, there are effects in that the microbe propagation in the object can be prevented, and the odor of the gas can be deodorized.

According to the twelfth aspect of the present invention, the ion supplying portion is provided to include the space to house the object in which the microbes can be propagated, and to supply the space with the ionic gas from which the ozone is removed by the ozone decomposing chamber. As a result, there is an effect in that the microbe propagation in the object can be prevented.

According to the thirteenth aspect of the present invention, the ion supplying portion is provided to include the space to house the object in which the microbes can be propagated, to supply the space with the ionic gas from which ozone is removed by the ozone decomposing chamber, and to return the gas supplied into the space to the ionization chamber. As a result, there are effects in that the microbe propagation in the object can be prevented, and the odor of the gas can be deodorized.

According to the fourteenth aspect of the present invention, the ionization chamber includes the pair of electrodes, and negative dc voltage is applied to the electrodes so as to ionize an electron. As a result, there are effects in that only the negative ion can be obtained, and a lifetime of the obtained ion can be extended.

According to the fifteenth aspect of the present invention, the ion supplying portion includes the space whose inner surface is made of the insulating material. As a result, there are effects in that the generating negative ion never decreases in the ion supplying portion, and the microbe propagation can be prevented.

According to the sixteenth aspect of the present invention, the ionic gas from which the ozone is removed by the ozone decomposing chamber is transformed into bubbles to be supplied into the water in the water reservoir. As a result, there is an effect in that the microbe propagation in the water can be reduced.

According to the seventeenth aspect of the present invention, the gas mixer is provided to mix ozone generated from the ozonizer with the gas ionized by the ionization chamber, and the diffusing apparatus is provided to transform the gas mixed by the gas mixer into bubbles so as to feed the bubbles into the water in the water reservoir. As a result, there are effects in that the microbe propagation in the water can be surely reduced because of the synergistic effect of the ion and the ozone, and the microbes can be sterilized.

According to the eighteenth aspect of the present invention, the diffusing apparatus includes the diffuser. As a result, there is an effect in that the microbe propagation in the water can be reduced.

According to the nineteenth aspect of the present invention, the gas-liquid mixer includes the ejector. As a result, there is an effect in that the microbe propagation in the water can be reduced.

According to the twentieth aspect of the present invention, the gas from which the ozone is removed by the ozone decomposing chamber is supplied into the space housing the object in which microbes can be propagated. As a result, there is an effect in that the microbe propagation in the object can be reduced.

According to the twenty-first aspect of the present invention, the gas from which ozone is removed by the ozone decomposing chamber is supplied into the space housing the object in which microbes can be propagated, and the gas supplied into the space is returned to the ionization chamber. As a result, there are effects in that the microbe propagation in the object can be prevented, and the odor of the gas can be deodorized.

According to the twenty-second aspect of the present invention, when the ionic gas from which the ozone is removed by the ozone decomposing chamber is supplied into the space, the ionic gas is intermittently supplied into the space. As a result, there are effects in that the microbe propagation can be reduced as in the case of continuous supplying, and cost can be reduced.

According to the twenty-third aspect of the present invention, when the ionic gas from which the ozone is removed by the ozone decomposing chamber is supplied into the space, the ionic gas is supplied after the gas is humidified. As a result, there are effects in that the microbe propagation can be reduced while drying of the object such as the food contained in the space can be prevented, and the foods or the like can be preserved for a long period.

According to the twenty-fourth aspect of the present invention, the wind blower draws the gas in the closed space which prevents the microbe propagation, and supplies the ionic gas from which the ozone is removed by the ozone decomposing chamber to the space. As a result, there is an effect in that the microbe propagation in the closed space can be reduced.

According to the twenty-fifth aspect of the present invention, the ionic gas from which the ozone is removed by the ozone decomposing chamber is supplied into the opened space or the liquid to prevent the microbe propagation, and the excess ion is removed from the space or the liquid. As a result, there are effects in that the excess ion supplied to the space or the liquid can be reduced while preventing the microbe propagation.

According to the twenty-sixth aspect of the present invention, the excess ion in the space or liquid is removed by the conductive net which is grounded. As a result, there is an effect in that the excess ion supplied to the space or the liquid can be reduced in a simple configuration requiring no replacement.

While preferred embodiments of the invention have been described using specific terms, such description is for illustrative purposes only, and it is to be understood that changes and variations may be made without departing from the spirit or scope of the following claims.

What is claimed is:

1. A microbe propagation preventing method comprising the steps of:

drawing a gas using a wind blower;

passing the gas through an air duct from an upstream position of the air duct to a downstream position of the air duct;

generating ions in said gas in an ionization chamber to form an ionized gas;

providing the ionized gas to an ozone decomposing chamber disposed downstream from said ionization chamber;

decomposing ozone in the ionized gas by the ozone decomposing chamber;

housing an object in an enclosed area in which microbes can propagate; and supplying the ionized gas without ozone to the enclosed area to prevent substantial microbe propagation.

2. A microbe propagation preventing method comprising the steps of:

drawing a gas using a wind blower;

passing the gas through an air duct from an upstream position of the air duct to a downstream position of the air duct;

generating ions in the gas using an ionization chamber to form an ionized gas;

providing the ionized gas to an ozone decomposing chamber disposed downstream from the ionization chamber;

decomposing ozone in the ionized gas using the ozone decomposing chamber; and providing a pair of conductive nets positioned perpendicular to a flow of the ionized gas and separated from one another by a predetermined distance for releasing only negative ions of the ionized gas into the ozone decomposing chamber to prevent substantial microbe propagation in the gas.

3. A microbe propagation preventing method according to claim 1 wherein the step of decomposing ozone includes the step of intermittently supplying the ionized gas to the ozone decomposing chamber.

4. A microbe propagation preventing method according to claim 2 wherein the step of decomposing ozone includes the step of intermittently supplying the ionized gas to the ozone decomposing chamber.

5. A microbe propagation preventing method according to claim 1, further comprising the step of:

humidifying the ionized gas after the step of decomposing ozone.

6. A microbe propagation preventing method according to claim 2, further comprising the step of:

humidifying the ionized gas after the step of decomposing ozone.

* * * * *

UNITED STATES PATENT AND TRADEMARK OFFICE
CERTIFICATE OF CORRECTION

PATENT NO. : 5,484,570
DATED : January 16, 1996
INVENTOR(S) : Akira Ikeda, et al It is certified that error appears in the above-indentified patent and that said Letters Patent is hereby corrected as shown below:

On the title page: Item [54] and Column 1, line 1,

In the Title change "PRENVENTION" to --PREVENTION --.

Signed and Sealed this

Sixteenth Day of April, 1996

Attest:

BRUCE LEHMAN

Attesting Officer

Commissioner of Patents and Trademarks